United States Patent
Giftakis et al.

(10) Patent No.: US 8,417,346 B2
(45) Date of Patent: Apr. 9, 2013

(54) ELECTRICAL STIMULATION OF ILIOHYPOGASTRIC NERVE TO ALLEVIATE CHRONIC PELVIC PAIN

(75) Inventors: Jonathon E. Giftakis, Maple Grove, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 383 days.

(21) Appl. No.: 12/815,084

(22) Filed: Jun. 14, 2010

(65) Prior Publication Data

US 2010/0249876 A1    Sep. 30, 2010

Related U.S. Application Data

(63) Continuation of application No. 11/414,614, filed on Apr. 28, 2006, now Pat. No. 7,761,166.

(51) Int. Cl.
*A61N 1/36* (2006.01)
(52) U.S. Cl. ............................................. 607/46
(58) Field of Classification Search .................. 600/347; 607/39, 45, 46
See application file for complete search history.

(56) References Cited

U.S. PATENT DOCUMENTS

| | | | |
|---|---|---|---|
| 5,501,703 A | 3/1996 | Holsheimer et al. | |
| 5,634,462 A | 6/1997 | Tyler et al. | |
| 5,660,854 A | 8/1997 | Haynes et al. | |
| 5,792,187 A | 8/1998 | Adams | |
| 6,169,924 B1 | 1/2001 | Meloy et al. | |
| 6,862,479 B1 | 3/2005 | Whitehurst et al. | |
| 6,885,895 B1 | 4/2005 | Whitehurst et al. | |
| 6,944,497 B2 | 9/2005 | Stypulkowski | |
| 7,292,890 B2 | 11/2007 | Whitehurst et al. | |
| 2002/0055761 A1 | 5/2002 | Mann et al. | |
| 2003/0004553 A1 | 1/2003 | Grill et al. | |
| 2003/0100930 A1 | 5/2003 | Cohen et al. | |
| 2003/0236557 A1 | 12/2003 | Whitehurst et al. | |
| 2004/0073197 A1 | 4/2004 | Kim | |
| 2004/0122477 A1 | 6/2004 | Whitehurst et al. | |
| 2004/0193228 A1 | 9/2004 | Gerber | |
| 2005/0010260 A1* | 1/2005 | Gerber ............................ 607/39 |
| 2005/0033372 A1 | 2/2005 | Gerber | |
| 2005/0033373 A1 | 2/2005 | Gerber | |
| 2005/0085486 A1 | 4/2005 | Gonzalez-Cadavid et al. | |
| 2005/0096709 A1 | 5/2005 | Skwarek et al. | |
| 2005/0113877 A1 | 5/2005 | Spinelli et al. | |
| 2005/0113878 A1 | 5/2005 | Gerber | |

(Continued)

OTHER PUBLICATIONS

Office Action dated Nov. 26, 2010 for U.S. Appl. No. 11/414,509, (8 pgs.).

(Continued)

*Primary Examiner* — Brian T Gedeon

(57) ABSTRACT

The disclosure describes a method and system for applying electrical stimulation to an iliohypogastric nerve of a patient. The system includes electrical stimulators that apply electrical stimulation for alleviation of pelvic pain. The system may apply electrical stimulation for pelvic pain in men or women. The electrical stimulators may comprise various types of electrodes such as cuff electrodes, electrode leads, and microstimulators implanted at various locations proximate to a single or both iliohypogastric nerves of a patient. In particular, the electrode may be implanted proximate or adjacent to an anterior cutaneous branch of one or both iliohypogastric nerves, a lateral cutaneous branch of one or both iliohypogastric nerves, or one or both of iliohypogastric nerves above the branch point.

26 Claims, 14 Drawing Sheets

U.S. PATENT DOCUMENTS

| | | | |
|---|---|---|---|
| 2005/0131484 | A1 | 6/2005 | Boveja et al. |
| 2005/0143789 | A1 | 6/2005 | Whitehurst et al. |
| 2005/0149345 | A1 | 7/2005 | Boggs, II et al. |
| 2005/0216069 | A1 | 9/2005 | Cohen et al. |
| 2005/0222628 | A1 | 10/2005 | Krakousky |
| 2005/0228451 | A1 | 10/2005 | Jaax et al. |
| 2006/0004429 | A1 | 1/2006 | Mrva et al. |
| 2006/0020297 | A1 | 1/2006 | Gerber et al. |
| 2006/0069415 | A1 | 3/2006 | Cameron et al. |
| 2006/0095088 | A1 | 5/2006 | De Ridder |
| 2006/0155344 | A1 | 7/2006 | Rezai et al. |
| 2006/0173507 | A1 | 8/2006 | Mrva et al. |
| 2007/0021801 | A1 | 1/2007 | Heruth et al. |
| 2007/0021802 | A1 | 1/2007 | Heruth et al. |
| 2007/0039625 | A1 | 2/2007 | Heruth et al. |
| 2007/0173900 | A1 | 7/2007 | Siegel et al. |

OTHER PUBLICATIONS

Request for Continued Examination (RCE) and Amendment dated Feb. 28, 2011 for U.S. Appl. No. 11/414,509 (18 pgs.).
U.S. Appl. No. 11/414,614, filed Apr. 28, 2006 entitled: "Electrical Stimulation of Iliohypogastric Nerve to Alleviate Chronic Pelvic Pain".
U.S. Appl. No. 11/413,617, filed Apr. 28, 2006 entitled: "Drug Deliveryto Alleviate Chronic Pelvic Pain".
U.S. Appl. No. 11/414,505, filed Apr. 28, 2006 entitled: "Drug Delivery to Iliohypogastric Nerve to Alleviate Chronic Pelvic Pain".
U.S. Appl. No. 11/344,580, filed Jan. 31, 2006 entitled: "Electrical Stimulation to Alleviate Chronic Pelvic Pain".
U.S. Appl. No. 11/413,621, filed Apr. 28, 2006 entitled: "Electrical Stimulation to Alleviate Chronic Pelvic Pain".
U.S. Appl. No. 11/414,615, filed Apr. 28, 2006 entitled: "Electrical Stimulation of Ilioinguinal Nerve to Alleviate Chronic Pelvic Pain".
Office Action dated Jun. 27, 2008 for U.S. Appl. No. 11/414,615 (20 pgs.).
U.S. Appl. No. 11/414,705, filed Apr. 28, 2006 entitled: "Drug Delivery to Ilioinguinal Nerve to Alleviate Chronic Pelvic Pain".
U.S. Appl. No. 11/414,509, filed Apr. 28, 2006 entitled: "Neuromodulation Therapy for Perineal or Dorsal Branch of Pudendal Nerve".
Responsive Amendment dated Dec. 22, 2008 for U.S. Appl. No. 11/413,621 (11 pgs.).
Responsive Amendment dated Sep. 29, 2008 for U.S. Appl. No. 11/414,615 (15 pgs.).
Office Action dated Jun. 30, 2008 for U.S. Appl. No. 11/414,705 (17 pgs.).
Responsive Amendment dated Sep. 29, 2008 for U.S. Appl. No. 11/414,705 (15 pgs.).
Office Action dated Sep. 22, 2008 for U.S. Appl. No. 11/413,621 (8 pgs.).
Office Action dated Mar. 12, 2010 for U.S. Appl. No. 11/414,615 (9 pgs.).
Request for Continued Examination and Responsive Amendment dated Jun. 8, 2010 for U.S. Appl. No. 11/414,615 (15 pgs.).
Office Action dated Jan. 9, 2009 for U.S. Appl. No. 11/414,615 (12 pgs.).
Responsive Amendment dated May 11, 2009 for U.S. Appl. No. 11/414,615 (11 pgs.).
Office Action dated Feb. 26, 2009 for U.S. Appl. No. 11/414,705 (9 pgs.).
Responsive Amendment dated May 26, 2009 for U.S. Appl. No. 11/414,705 (10 pgs.).
Office Action dated May 1, 2009 for U.S. Appl. No. 11/413,621 (10 pgs.).
Office Action dated Jul. 20, 2009 for U.S. Appl. No. 11/414,615 (8 pgs.).
Request for Continued Examination (RCE) and Responsive Amendment dated Oct. 1, 2009 for U.S. Appl. No. 11/413,621 (13 pgs.).
Response dated Oct. 20, 2009 for U.S. Appl. No. 11/414,615 (9 pgs.).
Office Action dated Dec. 11, 2009 for U.S. Appl. No. 11/413,621 (12 pgs.).
Responsive Amendment dated Mar. 4, 2010 for U.S. Appl. No. 11/413,621 (9 pgs.).
Office Action dated Jun. 14, 2010 for U.S. Appl. No. 11/414,509 (11 pgs.).
Responsive Amendment dated Sep. 14, 2010 for U.S. Appl. No. 11/414,509 (15 pgs.).
Office Action dated Jun. 28, 2010 for U.S. Appl. No. 11/414,615 (8 pgs.).
Murovic, J. A., Kim, D. H., Tiel, R. L., Kline, D. G., "Surgical Management of 10 Genitofemoral Neuralgias at the Louisiana State University Health Sciences Center," Neurosurgery, vol. 56, No. 2, pp. 298-303, www.neurosurgery-online.com, Feb. 2005.
Kim, D. H., Murovic, J. A., Tiel, R. L., Kline, D. G., "Surgical Management of 33 Ilioinguinal and Iliohypogastric Neuralgias at the Louisiana State University Health Sciences Center," Neurosurgery, vol. 56, No. 5, pp. 1013-1020,, www.neurosurgery-online.com, May 2005.
Brindley, G. S., "Sacral root and hypogastric plexus stimulators and what these models tell us about autonomic actions on the bladder and urethra," Clinical Science, vol. 70 (Suppl. 14), pp. 41s-44s, 1985.
Granitsiotis, P., Kirk, D.; "Chronic Testicular Pain: An Overview," European Urology, vol. 45, pp. 430-436, 2004.
Sasaoka, N., Kawaguchi, M., Yoshitani, K., Kato, H., Suzuki, A., Furuya, H., "Evaluation of genitofemoral nerve block, in addition to ilioinguinal and iliohypogastric nerve block, duting inguinal hernia repair in children", British Journal of Anaesthesia, vol. 94 No. 2, pp. 243-246, 2005.
Berman, J., Berman, L. "Female Sexual Function and Dysfunction", Annual Meeting of American Urological Association, Inc., May 29, 2002.
Yucel, S., Baskin, L. S., The neuroanatomy of the human scrotum:surgical ramifications:, BJU International, vol. 51, pp. 393-397, 2003.
Levine, L. A., Matkov, T. G., Microsurgical Denervation of the Spermatic Cord as Primary Surgical Treatment of Chronic Orchialgia, The Journal of Urology, vol. 165, pp. 1927-1929, Jun. 2001.
Gillitzer, R., Hampel, C., Wiesner, C., Pahernik, S., Melchior, S., Thuroff, J. W., "Pudendal Nerve Branch Injury During Radical Perineal Prostatectomy," Journal of Urololgy, vol. 67, No. 2, 2006.
Uchio, E. M., Yang, C. C., Kromm, B. G., Bradley, W. E., "Cortical Evoked Responses from the Perineal Nerve," The Journal of Urology, vol. 162, pp. 1983-1986, Dec. 1999.
The Pain Clinic, "Peripheral Nerve Blocks", http://www.painclinic.org/treatment-peripheralnerveblocks.htm, 2006, (10 pages).
Mayo Foundation for Medical Education and Research, "Urinary Incontinence", http://www.mayoclinic.com/health/urinaryincontinence/DS00404/DSECTION=8, 2006, (5 pages).
Mayo Foundation for Medical Education and Research, "Erectile Dysfunction", http://www.mayoclinic.com/health/erectiledysfunction/DS00162/DSECTION=7, Jan. 18, 2006, (3 pages).
New York School of Regional Anesthesia, "Genitofemoral Block", http://www.nysora.com/techniques/genitofemoral_block/, 2006, (3 pages).
Hruby et al., "Anatomy of pudendal nerve at urogenital diaphragm—new critical site for nerve entrapment", Journal of Urology, vol. 66, Issue 5, Nov. 2005, pp. 949-952.
Bolandard et al., European Society of Regional Anaesthesia and Pain Therapy, "Ilioinguinal-Iliohypogastric Block—Single Shot", 2006 (2 pages).
Responsive Amendment dated Sep. 28, 2010 for U.S. Appl. No. 11/414,615 (18 pgs.).
Office Action from U.S. Appl. No. 12/861,165, dated Aug. 29, 2012, 10 pp.
Response to Office Action dated Aug. 29, 2012, from U.S. Appl. No. 12/861,165, filed Nov. 29, 2012, 14 pp.

* cited by examiner

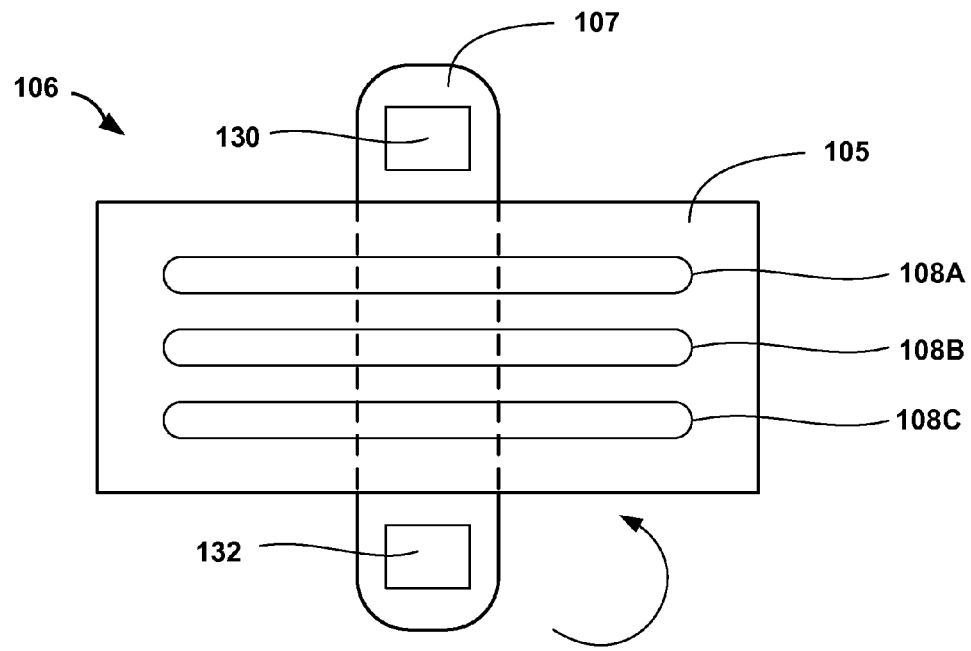
FIG. 10A
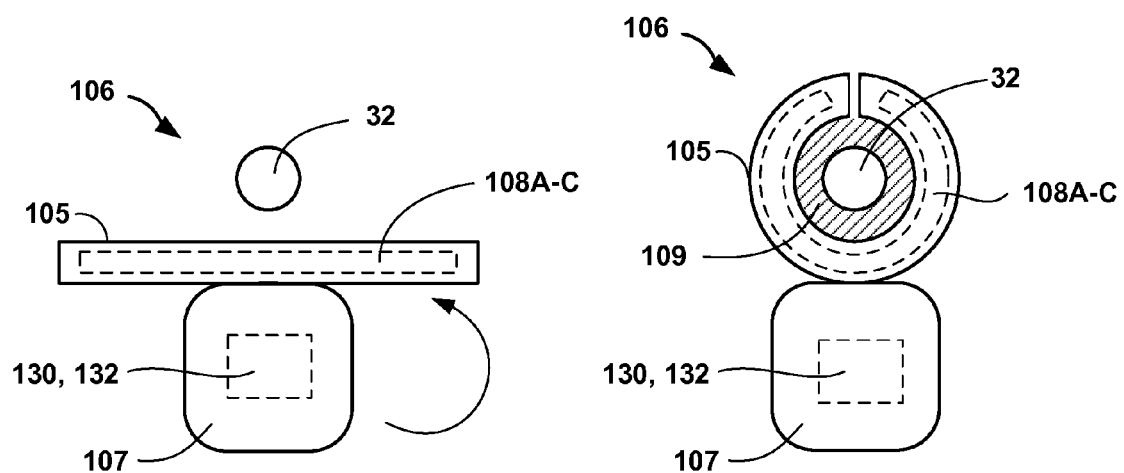
FIG. 10B
FIG. 10C

ELECTRICAL STIMULATION OF ILIOHYPOGASTRIC NERVE TO ALLEVIATE CHRONIC PELVIC PAIN

This application is a continuation of U.S. application Ser. No. 11/414,614, now U.S. Pat. No. 7,761,166, filed on Apr. 28, 2006, the entire content of which is incorporated herein by reference.

TECHNICAL FIELD

The invention relates to medical devices and, more particularly, to devices for delivering neurostimulation therapy.

BACKGROUND

Pain in the pelvic region, including urogential pain, may be caused by a variety of injuries or disorders in men and women. For example, iliohypogastric neuralgia, ilioinguinal neuralgia, genitofemoral neuralgia, chronic groin pain, chronic testicular pain (CTP), post vasectomy pain, and other pain originating from the testicles, groin, or abdomen are common reasons for referral to a urological specialist.

As an example, iliohypogastric, ilioinguinal, and genitofemoral neuralgia may be attributed to nerve injury, such as stretching of a nerve, electrocoagulation, stricture caused by ligation, entrapment of the nerve in scar tissue, or irritation because of proximity to a zone of inflammation, during inguinal herniorrhaphy. In addition to herniorrhaphy, other abdominal procedures that may cause these neuralgias or CTP include appendectomy, iliac crest bone graft harvesting, urological operations, and gynecological surgery, including transverse or paramedian incisions for hysterectomy. The pain experienced by the patient may be unilateral or bilateral, constant or intermittent, spontaneous or exacerbated by physical activities and pressure, and may remain localized in the scrotum or radiate to the groin, perineum, back, or legs.

Typically, denervation procedures are used to treat various neuralgias. In denervation procedures, the nerve that is diagnosed as the cause, e.g., using the results of the patient history, physical examination, preoperative electromyography, and nerve blocks, is severed or permanently removed. Such procedures may result in permanent and substantial pain relief regardless of the origin of pain. However, severing or removing some nerves may result in loss of sensation. Therapeutic nerve blocks may also be used to treat various neuralgias, but generally only relieve pain temporarily.

In addition, women may experience various types of sources of pelvic pain. Sources of pain may include injury to nerves resulting from surgical procedures, non-surgical conditions, vulvodynia which can be very debilitating but has no obvious source, and interstitial cystitis (painful bladder syndrome). Interstitial cystitis may be a source of pelvic pain in both women and men. Surgical procedures that may injure nerves in the pelvic region may include urological operations in the pelvic area, gynecological surgery, and hysterectomy. Non-surgical conditions which cause pain in women include adhesions, endometriosis, and pelvic congestion.

SUMMARY

In general, the invention is directed to techniques for applying electrical stimulation to an iliohypogastric nerve of a patient via an implantable electrical stimulation device to alleviate symptoms of chronic pelvic pain in men or women. Pelvic pain may include urogenital pain or other forms of pelvic pain. The electrical stimulation may be applied to one or both iliohypogastric nerves.

A system according to the invention may include one or more electrical stimulators that apply electrical stimulation to the iliohypogastric nerve to alleviate chronic groin pain or other afflictions associated with pelvic pain, including pain originating from the testicles, groin, or abdomen, such as post vasectomy pain and iliohypogastric neuralgia. In female patients, an electrical stimulator delivers the stimulation to the iliohypogastric nerve to alleviate other types of pelvic pain such as vulvodynia, interstitial cystitis, post-operative pain, adhesions, endometriosis or pelvic congestion.

The electrical stimulators may comprise various types of electrodes such as cuff electrodes, electrode leads, and/or microstimulators implanted at various locations proximate to one or both of the iliohypogastric nerves of a patient. For example, the electrical stimulators may be implanted proximate to the anterior cutaneous branch of one or both of the iliohypogastric nerves of a patient or the lateral cutaneous branch of one or both of the iliohypogastric nerves. The electrical stimulators may alternatively or additionally be implanted proximate to one or both of the iliohypogastric nerves above the branch point i.e., the point at which the iliohypogastric nerve branches to form the anterior cutaneous and lateral cutaneous branches. In this manner, stimulation may be applied uni-laterally (to one nerve or branch) or bi-laterally (to both cords or branches).

In some embodiments, electrical stimulation electrodes may be coupled to an implantable stimulation device implanted within a subcutaneous pocket in the abdomen of the patient or, alternatively, the scrotum or buttock of the patient. The electrical stimulation electrodes may be coupled to the implantable medical device via standard implantable electrode leads. Alternatively, leadless microstimulators may be positioned adjacent the target nerves. In this case, the leadless microstimulators may be capable of wireless communication with other implantable medical devices, an external programmer, or both.

For male patients, stimulation electrodes or leadless microstimulators may be implanted using well known surgical procedures such as those used in repairing an inguinal hernia, exposing the spermatic cord, or iliohypogastric denervation. Systems including such electrodes or microstimulators and employing the techniques described in this disclosure may substantially reduce or eliminate chronic pelvic pain, including urogenital pain such as chronic groin pain or iliohypogastric neuralgia, without loss of sensation in the thigh, penis, and/or scrotum.

Systems according to the invention may include an external programmer that programs the electrical stimulators to apply electrical stimulation to an iliohypogastric nerve. During stimulation, a clinician or patient may operate the external programmer to adjust stimulation parameters, such as amplitude, pulse width, pulse rate, and electrode polarities. In some cases, a patient may use the programmer to deliver stimulation on demand, e.g., when the patient experiences discomfort. Additionally or alternatively, the implantable stimulation device may store stimulation programs and schedules. In this manner, the electrical stimulation can be delivered according to preprogrammed stimulation parameters and schedules, if desired.

In one embodiment, the invention provides a method comprising applying electrical stimulation to an iliohypogastric nerve of a patient via an implanted electrical stimulation device.

In another embodiment, the invention provides a system comprising an implantable electrical stimulation device that generates electrical stimulation selected to alleviate pelvic pain, and an electrode coupled to the electrical stimulation device at a position adjacent to an iliohypogastric nerve of a patient.

In a further embodiment, the invention provides a method comprising applying electrical stimulation to at least a portion of an iliohypogastric nerve of a patient via an implanted electrical stimulation device.

In another embodiment, the invention provides a system comprising an implantable electrical stimulation device that generates electrical stimulation selected to alleviate pelvic pain, and an electrode coupled to the electrical stimulation device at a position adjacent to an iliohypogastric nerve of a patient.

In various embodiments, the invention may provide one or more advantages. For example, applying electrical stimulation to an iliohypogastric nerve of a patient may substantially reduce or eliminate pelvic pain such as that caused by chronic groin pain, post vasectomy pain, iliohypogastric neuralgia, and other conditions that cause long term pain in the testicles, groin, or abdomen, as well as other forms of pelvic pain experienced by female patients.

Iliohypogastric denervation procedures that sever or remove the iliohypogastric nerve often result in unwanted side effects including loss of sensation in thigh, penis, and/or scrotum. Therapeutic nerve blocks typically only relieve pain temporarily. In contrast, delivery of electrical stimulation to one or both iliohypogastric nerves may provide permanent or long-lived effective therapy for many patients with fewer or no unwanted side effects.

In addition, for male patients, electrical stimulators may be implanted proximate to the iliohypogastric nerve using well known surgical procedures for repairing an inguinal hernia, exposing the spermatic cord, or iliohypogastric denervation, thereby providing ease of deployment by experienced surgeons or other caregivers.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 10A, 10B and 10C are schematic diagrams illustrating an example leadless microstimulator suitable for use in the system of FIGS. 6 and 7.

DETAILED DESCRIPTION

Figure 1:
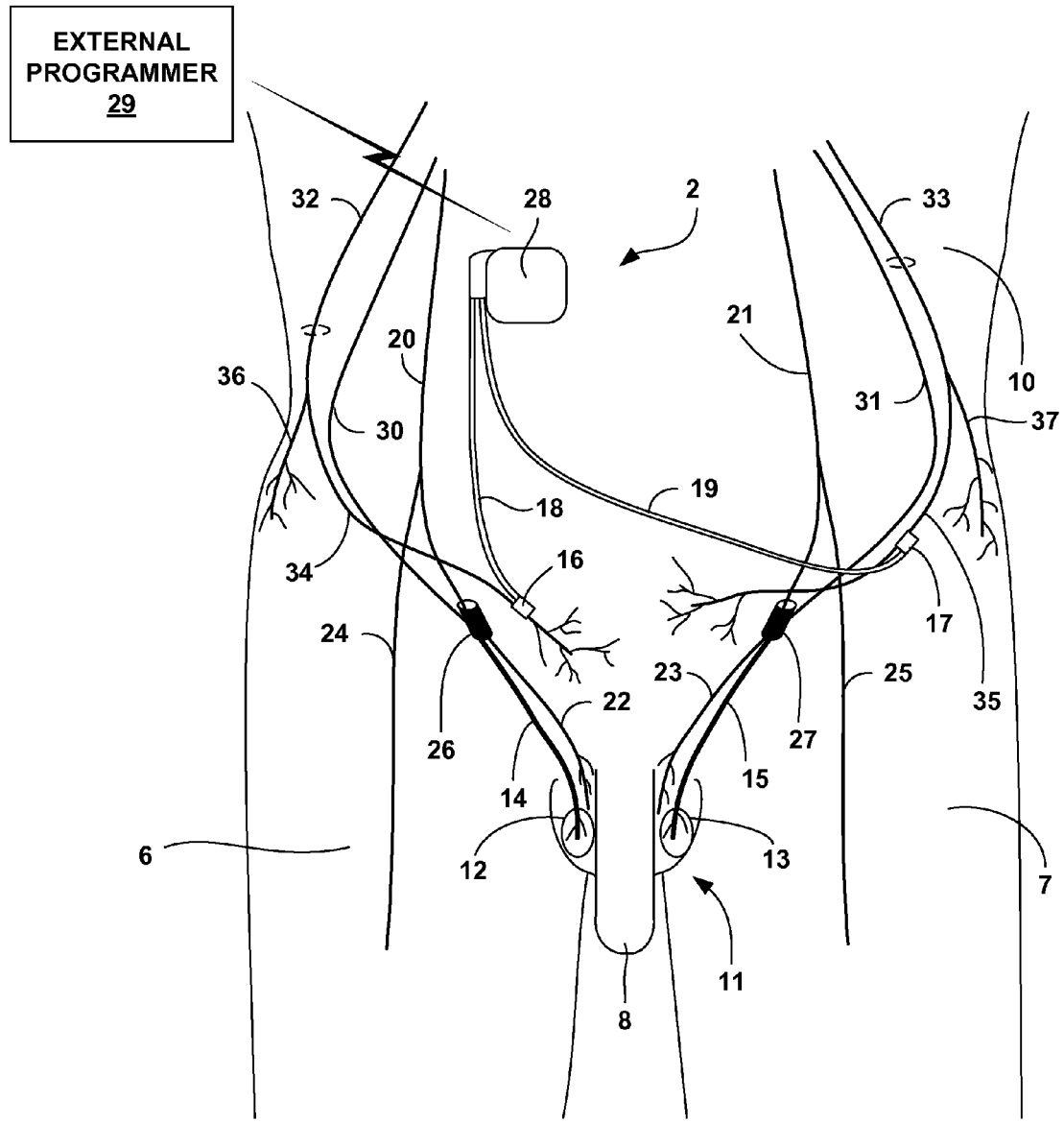
FIG. 1 is a schematic diagram illustrating an example system that includes an implantable stimulation device for applying electrical stimulation to an iliohypogastric nerve of a patient for alleviation of pelvic pain from a front view of a male patient.

FIG. 1 is a schematic diagram illustrating an example system 2 that includes an implantable medical device (IMD) 28 in the form of an electrical stimulator that applies electrical stimulation to one or both iliohypogastric nerves, the anterior cutaneous branch of one or both iliohypogastric nerves, or the lateral cutaneous branch of one or both iliohypogastric nerves of a patient 10. In FIG. 1, system 2 is illustrated from a front view perspective of patient 10. Although the invention may be generally applicable to treat pelvic pain in both men and women, application of the invention to men will be described throughout this disclosure for purposes of illustration. Throughout the figures accompanying this disclosure, various anatomical features of patient 10 and structural features of system 2 are illustrated conceptually for ease of illustration. Accordingly, the figures may not necessarily present appropriate scales and proportions of such anatomical features. Rather, the drawings are provided as a conceptual rendering of such features to aid in the understanding of pertinent embodiments of the invention.

In the example of FIG. 1, IMD 28 applies electrical stimulation to patient 10 for alleviation of chronic groin pain, post vasectomy pain, iliohypogastric neuralgia, or other conditions that cause long term (chronic) pain in the testicles (in a male patient), groin, or abdomen. As an example, chronic groin pain may be attributed to nerve injury, such as stretching of a nerve, electrocoagulation, stricture caused by ligation, entrapment of the nerve in scar tissue, or irritation proximate to a zone of inflammation during inguinal herniorrhaphy or other previous surgical interventions. In addition to herniorrhaphy, other abdominal procedures that may cause chronic groin pain or iliohypogastric neuralgia include appendectomy, iliac crest bone graft harvesting, and urological operations. In particular, damage to the iliohypogastric nerve may cause a patient to experience pain in the thigh, penis, and/or associated scrotal area. IMD 28 may also deliver stimulation to patient 10 for alleviation of chronic pelvic pain that is idiopathic in origin. Stimulation parameters such as amplitude, pulse width and pulse rate may be selected as appropriate to alleviate pain for the particular patient 10.

In additional embodiments, IMD 28 applies electrical stimulation to a female patient (not shown) for alleviation of pelvic pain such as, urogenital pain and idiopathic pain. Examples of pain include pain resulting from surgical procedures, non-surgical procedures, vulvodynia, and interstitial cystitis (painful bladder syndrome). Nerve injury may be caused by various surgical procedures including urological operations in the pelvic area, gynecological surgery, and hysterectomy. Non-surgical conditions which cause pain in women include adhesions, endometriosis, and pelvic congestion. Applying electrical stimulation to the anterior or lateral cutaneous branch of the iliohypogastric nerve or to the iliohypogastric nerve above the branch point in accordance with selected stimulation parameters may alleviate pain experienced by female patients.

FIG. 1 illustrates anterior cutaneous branches 34, 35 and lateral cutaneous branches 36, 37 of iliohypogastric nerves 32, 33, respectively. In addition, FIG. 1 illustrates other nerves in the inguinal region of patient 10, e.g., ilioinguinal nerves 30, 31 and genital branches 22, 23 and femoral branches 24, 25 of genitofemoral nerves 20, 21, respectively. Spermatic cords 14, 15 include a portion of genital branches 22, 23, of genitofemoral nerves 20, 21, respectively. Generally, IMD 28 delivers electrical stimulation to anterior cutaneous branches 34, 35 of iliohypogastric nerves 32, 33 via electrodes which may be coupled to IMD 28 by one or more leads. The electrical stimulation has parameters selected to block pain signals from the abdomen and, in some cases, testicles 12 and 13, and/or the associated scrotal area 11 from reaching the central nervous system (CNS). As shown in the illustrated example of FIG. 1, the electrodes may be configured to at least partially engage a portion of the anterior cutaneous branches 34, 35. However, the invention is not so limited. Rather, the invention also includes embodiments in which electrodes may be implanted proximate to lateral cutaneous branches 36, 37 or iliohypogastric nerves 32, 33, i.e., above the branch point of anterior cutaneous branches 34, 35, respectively. In the illustrated example of FIG. 1, a dotted circle indicates an example stimulation site along iliohypogastric nerves 32, 33.

Further, the invention includes embodiments in which an electrode is implanted proximate to at least one of iliohypogastric nerve 32, iliohypogastric nerve 33, anterior cutaneous branch 34, anterior cutaneous branch 35, lateral cutaneous branch 36, and lateral cutaneous branch 37. For example, electrodes may be implanted proximate to iliohypogastric nerve 32 and proximate to anterior cutaneous branch 34. In another example, electrodes may be implanted proximate to iliohypogastric nerve 32 and proximate to lateral cutaneous branch 36. In yet another example, electrodes may be implanted proximate to anterior cutaneous branch 34 and proximate to lateral cutaneous branch 36. The invention further includes embodiments in which electrodes are implanted bi-laterally in any combination. Such embodiments are included without exhaustively listing all possible combinations. Accordingly, the positions of electrodes 16 and 17 in FIG. 1 are merely exemplary.

The pain experienced by the patient may be unilateral or bilateral, constant or intermittent, spontaneous or exacerbated by physical activities and pressure, and may remain localized or radiate outward. In a male patient, for example, pain may remain localized in the penis, or radiate to the scrotum, thighs, perineum, or back. Delivering electrical stimulation may cause paresthesia in penis 8, thighs 6, 7, testicles 12 and 13 and associated scrotal region 11 based on the position of the electrodes. The number and position of the leads may be dependent on the pain perceived by the patient and the type of electrical stimulation delivered to treat the pain. Additionally, the leads coupled to IMD 28 may include various types of electrodes depending on the type of stimulation delivered and the location of the lead.

In the illustrated example, IMD 28 is coupled to leads 18 and 19. Leads 18 and 19 each include a cuff electrode, i.e., cuff electrodes 16 and 17, that delivers electrical stimulation therapy to iliohypogastric nerves 32 and 33, respectively. A cuff electrode includes a cuff-like fixation structure and one or more electrodes carried by the fixation structure. In the example of FIG. 1, leads 18 and 19 are implanted at different locations along iliohypogastric nerves 32 and 33, respectively. As a result, patient 10 may experience paresthesia in different areas on each side of his body in response to electrical stimulation delivered by electrodes 16 and 17.

Although cuff electrodes are shown in FIG. 1, the leads coupled to IMD 28 may include various types of electrodes depending on the type of stimulation delivered and the location of the lead. For example, IMD 28 may be coupled to any number and any type of electrodes, such as conventional ring electrode leads, paddle electrode leads, and other electrodes suitable for delivering electrical stimulation to iliohypogastric nerves 32, 33. In addition, in some cases, leadless stimulators may be used. A cuff electrode may provide more direct electrical contact, i.e., better electrical coupling, with an iliohypogastric nerve than a standard electrode lead. However, in some cases, applying electrical stimulation directly to a nerve may result in the patient experiencing an unpleasant sensation, such as a burning sensation. Consequently, a standard electrode implanted proximate to the iliohypogastric nerve lead may be advantageous because the patient may experience a more pleasant paresthesia as a result of stimulation. In addition, a standard electrode lead may also be advantageous in terms of surgical ease.

Figure 6:
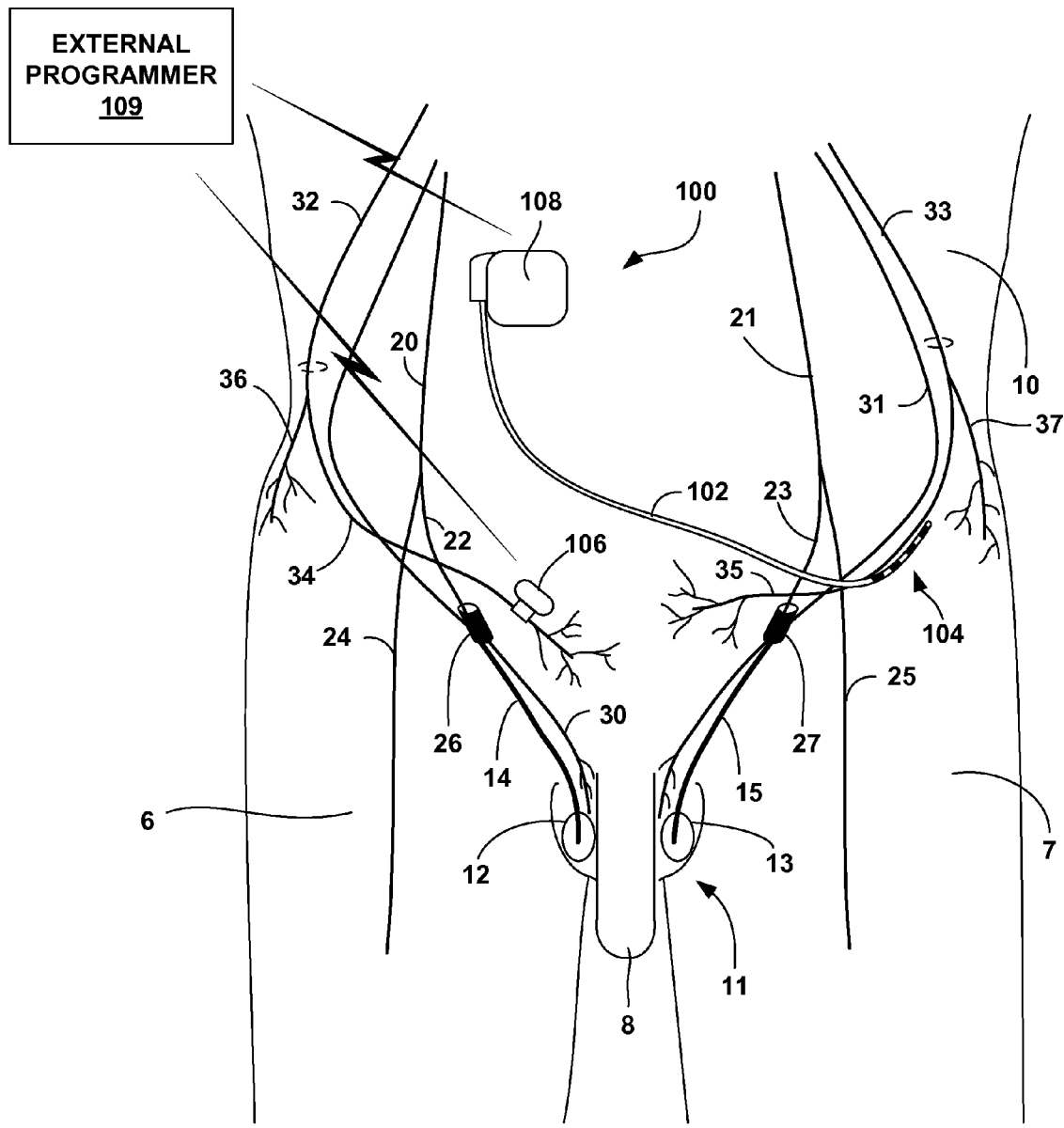
FIG. 6 is a schematic diagram illustrating another example system including two different types of electrical stimulators for applying electrical stimulation to an iliohypogastric nerve of a patient from a front view of a male patient.

As an example, FIG. 6 illustrates another system in which an IMD is coupled to an electrode lead having electrodes on the distal end of the lead to stimulate an iliohypogastric nerve of a patient. FIG. 6 also illustrates a leadless microstimulator implanted within the tissue adjacent to the iliohypogastric nerve. In this case, an IMD or external programmer may wirelessly control the leadless microstimulator to deliver electrical stimulation to the adjacent tissue. In addition, although not illustrated, an IMD may also be coupled to an electrode suitable for applying electrical stimulation to genital branches 22, 23 and/or femoral branches 24, 25, of genitofemoral nerves 20, 21 or ilioinguinal nerves 30, 31.

With further reference to FIG. 1, IMD 28 may be coupled to deliver electrical stimulation energy to iliohypogastric nerves 32, 33 via cuff electrodes 16, 17, respectively. Cuff electrodes 16 and 17 each may comprise a rigid or flexible cuff electrode, a self-sizing spiral cuff electrode, a half cuff electrode, a helical electrode, a chambered electrode, or other types of cuff electrodes that are shaped, sized and otherwise configured to at least partially wrap around an iliohypogastric nerve. The cuff electrode may be sized and shaped to at least partially enclose the iliohypogastric nerve and promote electrical coupling pressure between the electrode and the iliohypogastric nerve. The cuff electrodes 16, 17 may each include a single electrode or multiple electrodes. For example, a cuff electrode 16, 17 may include a bipolar or multipolar arrangement of electrodes or a unipolar electrode that is referenced to the electrical potential of an active can electrode carried by IMD 28.

IMD 28 includes electrical stimulation pulse generator circuitry and delivers electrical stimulation in the form of electrical pulses in accordance with stored stimulation parameters, e.g., electrode combination, electrode polarity, pulse amplitudes, pulse widths, pulse rates, and/or duty cycle. By way of example, the electrical stimulation may include stimulation pulses having pulse widths between approximately 10 and 5000 microseconds, more preferably between approximately 100 and 1000 microseconds, and still more preferably between 180 and 450 microseconds. The stimulation pulses may define voltage amplitudes between approximately 0.1 and 50 volts, more preferably between approximately 0.5 and 20 volts, and still more preferably between approximately 1 and 10 volts. The pulses may have frequencies between approximately 0.5 and 500 hertz, more preferably between approximately 10 and 250 hertz, and still more preferably between approximately 50 and 150 hertz. The pulses may be alternating current (ac) pulses or direct current (dc) pulses, and may be mono-phasic, bi-phasic, or multi-phasic in various embodiments.

IMD 28 may drive electrodes 16 and 17 with the same or different stimulation pulses or waveforms. In some embodiments, IMD 28 may cause electrodes 16 and 17 to deliver electrical stimulation simultaneously, or in an interleaved or alternating fashion. For example, electrodes 16 and 17 may deliver electrical stimulation with different pulse rates, duty cycles or scheduled times for delivery, which may result in alternating delivery of stimulation. Interleaved or alternating delivery of stimulation may, for example, reduce the likelihood that neural accommodation or tolerance will impair the efficacy of the stimulation. Interleaved or alternating delivery of stimulation may also result in more complete pain relief than would be possible through delivery of stimulation via only one electrode or electrode array. Interleaved stimulation may be delivered via conventional ring electrodes, paddle lead electrodes, cuff electrodes, microstimulators, or the like.

Leads 18 and 19 may be implanted proximate to iliohypogastric nerves 32, 33, respectively. In the illustrated example, lead 18 is implanted proximate to a region of iliohypogastric nerve 32 and lead 19 is implanted proximate to a different region of iliohypogastric nerve 32. Specifically, lead 18 is implanted proximate to a subcutaneous region of iliohypogastric nerve 32 located between the transverses and internal oblique muscles and lead 19 is implanted proximate to a cutaneous region of iliohypogastric nerve 33 after piercing the internal oblique by perforating the aponeurosis of the external oblique approximately 2.5 cm above the subcutaneous inguinal ring. However, the invention is not limited as such. Rather, lead 18 may be implanted at various locations along iliohypogastric nerves 32, 33, including anterior cutaneous branches 34, 35 and lateral cutaneous branches 36, 37 of iliohypogastric nerves 32, 33, respectively, or sympathetic nerves (not shown). The positions of leads 18 and 19 in FIG. 1 are shown for purposes of illustration to show different possible implantation locations and associated target stimulation sites. Specifically, leads 18 and 19 illustrate two locations which may be particularly advantageous for applying electrical stimulation, which will be described in detail below. However, IMD 28 may be coupled to a single lead or a plurality of leads based on the perceived pain of the patient and his response to electrical stimulation therapy.

The following is a general anatomical description of the iliohypogastric, ilioinguinal, and genitofemoral nerves that may be used for reference. However, the iliohypogastric, ilioinguinal, and genitofemoral nerves have been demonstrated to have a variable origin, course, and distribution in the inguinal region among different patients. In other words, anatomical variability may be observed from patient to patient. Accordingly, the drawings are provided as a conceptual representation to aid in the understanding of pertinent embodiments of the invention, but not necessarily as an accurate anatomical guide.

In FIG. 1, iliohypogastric nerves 32, 33, ilioinguinal nerves 30, 31, and genital branches 22, 23 and femoral branches 24, 25 of genitofemoral nerves 20, 21 are illustrated. FIG. 1 also illustrates inguinal canals 26 and 27. Although not explicitly shown in FIG. 1, the ilioinguinal nerves 30, 31 originate from the L1 and T12 nerves and also, in some cases, the L2 nerve. Generally, the ilioinguinal nerves run subperitoneally below the respective iliohypogastric nerves. The ilioinguinal nerves emerge from the lateral border of the psoas muscle (not shown) and pierce the transverses abdominis muscle (not shown) approximately one centimeter (cm) above the anterior superior iliac spine (not shown) and then cross the internal abdominal oblique muscle (not shown). The ilioinguinal nerves continue beneath the aponeurosis of the external oblique abdominal muscle (not shown) in the direction of the symphysis and pubic region.

The ilioinguinal nerves then lie medially, or less frequently, below or lateral to the spermatic cord in men or to the round ligament of the uterus in women and accompany the spermatic cord for approximately two to four centimeters through the respective inguinal canal ring 26, 27 through the internal inguinal ring. Often, the ilioinguinal nerve has a reciprocal relationship with regard to the diameter of the iliohypogastric nerve. In some cases, branches of the ilioinguinal nerves fan out and innervate the respective spermatic cord. Branches of the ilioinguinal nerves may pierce the oblique muscle aponeurosis to supply the sensory distribution to the skin of the superomedial thigh as well as to the root of the penis and the scrotum in men and to the skin of the mons pubis and labia majora in women.

For reference, the iliohypogastric nerves 32, 33 originate from the anterior branch of the L1 nerve and, frequently, the T12 nerve. The iliohypogastric nerves emerge along the lateral margin of the psoas muscle (not shown) to pass anterior to the quadratus lumborum (not shown). The iliohypogastric nerves perforate the transverses abdominis muscle (not shown) above the iliac crest (not shown) as in the ilioinguinal nerves. Approximately three centimeters to the anterior superior iliac spine, the iliohypogastric nerves may be found between layers of the transversus and internal oblique muscles (not shown). The iliohypogastric nerves divide between the transverus abdominis muscle and the internal oblique muscle into lateral and cutaneous branches.

The lateral cutaneous branch pierces the internal and external oblique muscles. The lateral cutaneous branch is then distributed to the skin of the gluteal region. The anterior cutaneous branch continues between the transverses and internal oblique muscles. In FIG. 1, electrode 16 is illustrated as being implanted proximate to anterior cutaneous branch 34 within this region. The anterior cutaneous branch pierces the internal oblique muscle and becomes cutaneous by perforating the aponeurosis of the external oblique approximately two to three centimeters above the internal ring of the inguinal canal and is distributed to the skin of the hypogastric region, i.e., the skin of the superomedial thigh, root of the penis, testicles, and associated scrotal region. Electrode 17 is illustrated as being implanted within this region of anterior cutaneous branch 35 in FIG. 1.

Genitofemoral nerves 20, 21 originate from the L1 and L2 nerves in the lumbar region (lower back) at L1/L2. As the genitofemoral nerves pass through the lumbar region, the genitofemoral nerves cross behind the ureter (not shown). Slightly posterior to and at a variable distance above the inguinal ligament (not shown), the genitofemoral nerves divide into genital branches and femoral branches. The genital branches cross the transverses abdominus (not shown) and internal oblique muscles (not shown) and enter the respective inguinal canals through the internal inguinal ring.

Within the inguinal canal, genital branches run along the respective spermatic cord. The spermatic cord includes various layers (not shown). These layers are the external spermatic fascia, cremasteric muscle and fascia, ilioinguinal nerve (in some cases), internal spermatic fascia, ductus deferens, lymph vessels, pampiniform plexus of veins which become the testicular vein, and testicular artery. More specifically, as the structures within the spermatic cord pass through the transversalis fascia (not shown), they join with one of the layers of the spermatic cord, the internal spermatic fascia.

In a male patient, as the spermatic cord continues through the inguinal canal, it joins with the cremasteric layer of muscle and fascia from the internal oblique muscle. These muscle fibers perform an important reflex, i.e., the cremasteric reflex. When the cremasteric muscle contracts, the testicle is pulled closer to the body. This reflex keeps the testicles at the correct temperature, for example, by relaxing when the testicles are too warm and contracting when the testicles are too cold. If the cremasteric reflex is absent or functions incorrectly, e.g., due to denervation or resection, the male may experience fertility related issues.

Finally, when the spermatic cord passes through the superficial ring, it joins an external spermatic fascia layer derived from the aponeurosis of the external oblique. After the spermatic cord traverses the inguinal canal, it leads into the scrotum and to the testes where the genital braches of the genitofemoral nerves innervate the testes.

In the illustrated example, cuff electrode 16 is wrapped around a subcutaneous portion of anterior cutaneous branch 34 of iliohypogastric nerve 32 and is connected to IMD 28 via lead 18 and, optionally, a lead extension (not shown). The electrical stimulation applied by cuff electrode 16 stimulates anterior cutaneous branch 34 of iliohypogastric nerve 30.

Electrode 17, in the illustrated example, also comprises a cuff electrode. More specifically, cuff electrode 17 is wrapped around a cutaneous portion of anterior cutaneous branch 35 of iliohypogastric nerve 33. Because cuff electrode 16 is located higher (upstream in the central nervous system) from cuff electrode 17, patient 10 may experience paresthesia over a larger area, which may be advantageous in some instances. Iliohypogastric nerves 32, 33, however, may not include an external fascia or other tissue to serve as a protective layer. Consequently, wrapping cuff electrodes 16 and 17 around iliohypogastric nerves 32 and 33 may inherently have a risk of pinching or otherwise damaging the nerve, possibly reducing the long-term efficacy of the electrical stimulation. As a result, care may be necessary when wrapping a cuff electrode around an iliohypogastric nerve.

The positions of electrodes 16, 17 in FIG. 1 are for purposes of illustration of different possible positions. In practice, one or both electrodes 16, 17 may be positioned within a subcutaneous region or anterior region of the nerve. Alternatively, one or both electrodes 16, 17 may be positioned within a cutaneous or distal end of the nerve. As discussed previously, electrodes may be positioned based on the pain perceived by the patient and the type of electrical stimulation delivered to treat the pain. In general, electrodes may be implanted proximate to a portion of the iliohypogastric nerve to apply electrical stimulation for treatment of chronic groin pain or iliohypogastric neuralgia.

In general, it may be difficult to wrap a cuff electrode around the iliohypogastric nerve within a subcutaneous region of the anterior cutaneous branch. Consequently, stimulation of the anterior cutaneous branch may preferably be applied to a cutaneous portion of the anterior cutaneous branch located at a more distal end of the iliohypogastric nerve. Additionally or alternatively, stimulation may be applied to the iliohypogastric nerve above (superior) the branch point of the nerve, i.e., before the nerve branches into the anterior and lateral cutaneous branches. Stimulation may also be applied to a lateral cutaneous branch of the iliohypogastric nerve depending on the pain experienced by the patient Leads 18 and 19 are typically either surgically implanted or inserted percutaneously. Leads 18 and 19 may be surgically implanted using well known surgical techniques. For example, the surgical procedure for neurectomy of the iliohypogastric nerve is well defined, i.e., an abdominal incision as used for neurectomy of the iliohypogastric nerve or hernia repair to expose the iliohypogastric and/or ilioinguinal nerve at the point of muscle emergence. A surgical procedure for iliohypogastric and ilioinguinal neurectomy is described in detail in Judith A. Murovic et. al, "Surgical Management of 33 Ilioinguinal and Iliohypogastric Neuralgias at the Louisiana State University Health Sciences Center," Neurosurgery, Volume 56, Number 5, pages 1013-1020, May 2005. Prior to surgically implanting electrodes, local nerve blocks may be performed using a nerve blocking agent to determine the precise nerve involved in the pain experienced by the patient. If an iliohypogastric nerve block ameliorates the patient's pain, a surgeon may conclude that electrical nerve stimulation is likely to be efficacious, and may proceed to surgically implant electrodes in accordance with the invention. Alternatively, a clinician may stimulate the patient using an insulated needle to determine the nerve involved and the placement of an electrode. The diagnosis may also be made using the results of the patient history, physical examination, and preoperative electromyography.

IMD 28 may be implanted at a site in patient 10 near iliohypogastric nerves 32 and 33. The implantation site may be a subcutaneous location in the side of the lower abdomen. Alternatively, IMD 28 may be implanted within the scrotum or buttock of the patient. IMD 28 may be miniaturized to allow IMD 28 to be implanted within the scrotum. In any case, the surgeon may then tunnel a lead through tissue and subsequently connect the lead to IMD 28, with or without a lead extension. IMD 28 may be constructed with a biocompatible housing, such as titanium or stainless steel, much like a conventional neurostimulator such as those used for spinal cord stimulation or pelvic stimulation, e.g., for relief of chronic pain, sexual dysfunction, or urinary or fecal incontinence.

External programmer 29 may control delivery of electrical stimulation by IMD 28. For example, in some embodiments, external programmer 28 may comprise a clinician programmer or a patient programmer. A clinician programmer may be a handheld computing device including a display, such as an LCD or LED display, to display electrical stimulation parameters. A clinician programmer may also include a keypad, which may be used by a user to interact with the clinician programmer. In some embodiments, the display may be a touch screen display, and a user may interact with the clinician programmer via the display. A user may also interact with the clinician programmer using peripheral pointing devices, such as a stylus or mouse. The keypad may take the form of an alphanumeric keypad or a reduced set of keys associated with particular functions.

A clinician (not shown) may use the clinician programmer to program electrical stimulation to be delivered to patient 10. In particular, the clinician may use the clinician programmer to select values for therapy parameters, such as pulse amplitude, pulse width, pulse rate, electrode polarity and duty cycle, for one of or both electrodes 16 and 17. IMD 28 may deliver the electrical stimulation according to programs, each program including values for a plurality of such therapy parameters. In this manner, IMD 28 controls delivery of electrical stimulation according to preprogrammed stimulation programs and schedules.

When implemented as a patient programmer, external programmer 29 may be a handheld computing device. The patient programmer 26 may also include a display and a keypad to allow patient 10 to interact with the patient programmer. In some embodiments, the display may be a touch screen display, and patient 10 may interact with the patient programmer via the display. Patient 10 may also interact with the patient programmer using peripheral pointing devices, such as a stylus or mouse.

Patient 10 may use the patient programmer to control the delivery of electrical stimulation. In particular, in response to a command from patient 10, external programmer 29 may activate IMD 28 to deliver electrical stimulation or, alternatively, deactivate IMD 28 when no electrical stimulation is desired. Patient 10 may also use the patient programmer to select the programs that will be used by IMD 28 to deliver electrical stimulation. Further, patient 10 may use the patient programmer to make adjustments to programs, such as adjustments to amplitude, pulse width and/or pulse rate. Additionally, the clinician or patient 10 may use a clinician or patient programmer to create or adjust schedules for delivery of electrical stimulation.

IMD 28 and external programmer 29, implemented as a clinician programmer or a patient programmer, communicate via wireless communication. In some embodiments, external programmer 29 communicates via wireless communication with IMD 28 using radio frequency (RF) telemetry techniques known in the art. The clinician programmer and patient programmer may communicate with one another by wireless communication, e.g., to change or update programs. Alternatively, the programmers may communicate via a wired connection, such as via a serial communication cable, or via exchange of removable media, such as magnetic or optical disks, or memory cards.

As previously described, leads 18 and 19 may be implanted surgically or percutaneously. When inserted percutaneously, leads 18 and 19 may be used in conjunction with an external trial stimulator (not shown) in order to determine if permanent implantation of the electrodes and leads is an effective treatment for the patient's pain. For example, prior to implantation of IMD 28, patient 10 may engage in a trial period, in which patient 10 receives an external trial stimulator on a temporary basis. The external trial stimulator is coupled to temporary leads or implanted leads via a percutaneous lead extension.

The trial neurostimulation permits a clinician to observe neurostimulation efficacy and determine whether implantation of a chronic neurostimulation device is advisable. Specifically, the trial neurostimulation period may assist the clinician in selecting values for a number of programmable parameters in order to define the neurostimulation therapy delivered to patient 10. For example, the clinician may select an amplitude, which may be current- or voltage-controlled, and pulse width for a stimulation waveform to be delivered to patient 10, as well as a rate, i.e., frequency) delivered to the patient. In addition, the clinician also selects particular electrodes on a lead to be used to deliver the pulses, and the polarities of the selected electrodes.

By stimulating iliohypogastric nerves 32 and 33, a system in accordance with an embodiment of the invention may substantially reduce or eliminate pelvic pain such as chronic groin pain, post vasectomy pain, iliohypogastric neuralgia, and other conditions that cause long term pain in the testicles, groin, or abdomen. Iliohypogastric denervation procedures may result in permanent and substantial pain relief but may also cause unwanted side effects, such as loss of sensation in the skin of the superomedial thigh, penis, testicle and/or scrotum. Therapeutic nerve blocks may also be used to treat iliohypogastric neuralgia, but generally only relieve pain temporarily. Because electrical stimulation does not require severing the iliohypogastric nerves cord and, more particularly, aims to avoid damaging nerves, the invention may provide similar or improved pain relief without the unwanted side effects.

Figure 2:
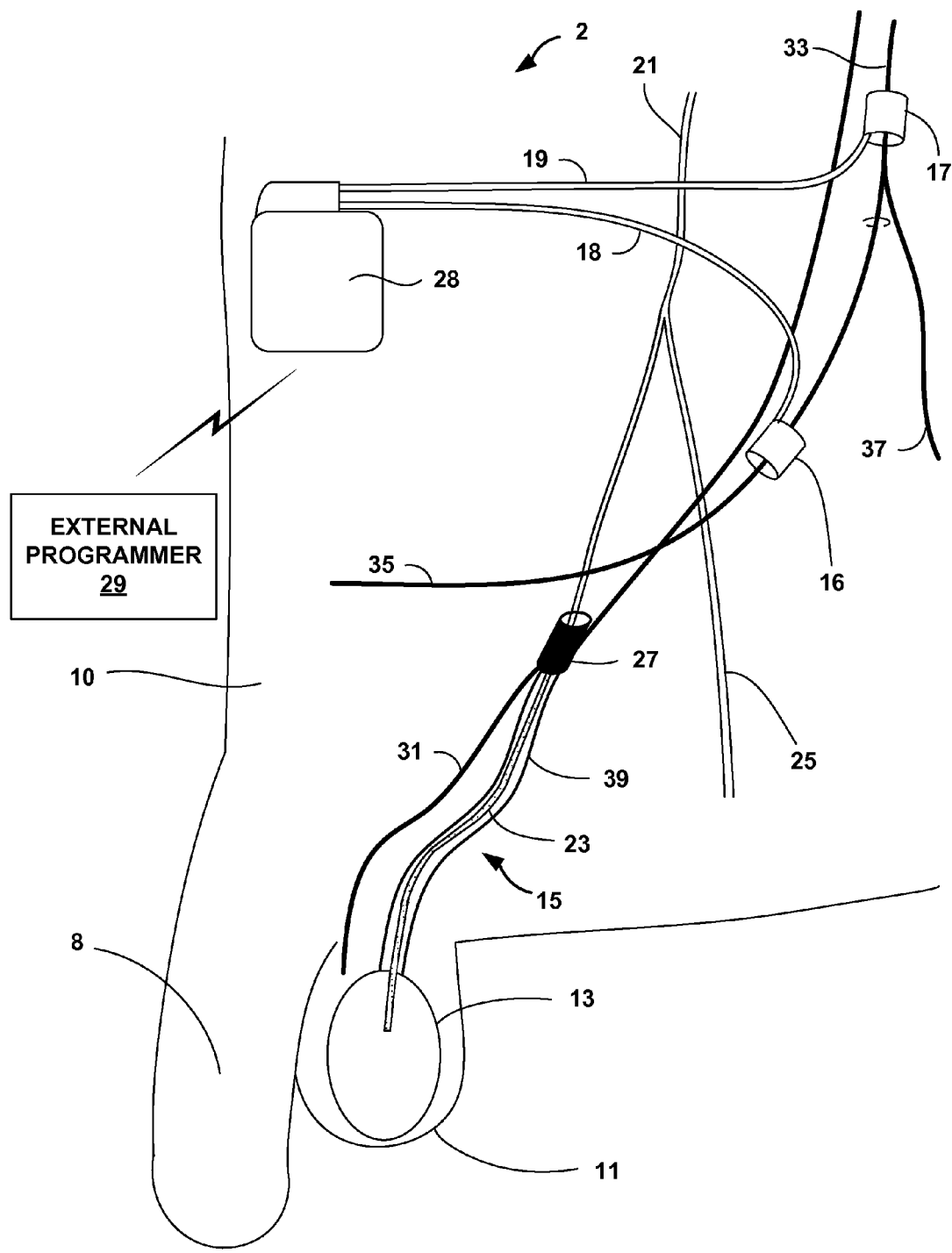
FIG. 2 is a schematic diagram further illustrating the example system of FIG. 1 from a side view of a male patient.

FIG. 2 is a schematic diagram further illustrating system 2. In particular, system 2 is illustrated from the left side of patient 10. For purposes of illustration, only iliohypogastric nerve 33, anterior cutaneous branch 35 and lateral cutaneous branch 37 of iliohypogastric nerve 33, genitofemoral nerve 21, genital nerve branch 23 and femoral nerve branch 25 of genitofemoral nerve 21, spermatic cord 15, external fascia layer 39, inguinal canal 27, testicle 13 and scrotum 11 are shown. In FIG. 2, cuff electrode 16 is illustrated as being wrapped around anterior cutaneous branch 35 of iliohypogastric nerve 33 below the branch point to illustrate the different locations at which electrodes may be implanted and to illustrate an embodiment in which multiple electrodes are implanted along iliohypogastric nerve 33. Accordingly, an additional cuff electrode 17 is shown as being wrapped around a portion of iliohypogastric nerve 33 above the branch point of iliohypogastric nerve 33, while cuff electrode 16 is shown as being wrapped around a different portion of anterior cutaneous branch 35 of iliohypogastric nerve 33. Following the convention illustrated in FIG. 1, a dotted circle illustrates an example stimulation site at which an electrode may be implanted on anterior cutaneous branch 35 at a position proximate to lateral cutaneous branch 37 of iliohypogastric nerve 33 in combination with one or more of electrodes 16 and 17.

In an embodiment in which two or more electrodes are implanted along the same iliohypogastric nerve 33, the electrodes may form a bipolar pair that is referenced between two electrodes deployed by leads 18, 19, or be individually referenced to an electrical potential associated with an electrode on the housing of IMD 28. Also, in some embodiments, multiple cuffs or leads may be implanted along iliohypogastric nerve 33, and each may carry multiple electrodes, e.g., in an axial or planar array, providing still more possible electrode combinations for selection by a physician.

FIG. 2 illustrates iliohypogastric nerve 33 branching to anterior cutaneous branch 35 to innervate the skin of the hypogastric region of patient 10 and lateral cutaneous branch 37 to innervate the skin of the gluteal region of patient 10. In particular, anterior cutaneous branch 35 may innervate portions or regions of penis 8, scrotum 11, and the abdomen of patient 10. Although not shown, branches of iliohypogastric nerve 33 may innervate ilioinguinal nerve 31 in some cases. As shown in FIG. 2, genital nerve branch 23 originates from genitofemoral nerve 21 and passes through inguinal canal 27 to innervate testicle 13. As previously described, spermatic cord 15 joins an external fascia layer 39 as it passes through the superficial ring of inguinal canal 27.

Cuff electrode 16 is wrapped around an anterior portion of anterior cutaneous branch 35, i.e., a subcutaneous portion of anterior cutaneous branch 35 between the transverses and internal oblique muscles. Optionally, another electrode is provided. For example, cuff electrode 17 is wrapped around a portion of iliohypogastric nerve 33 above the branch point of iliohypogastric nerve 33, i.e., a portion of iliohypogastric nerve 33 before branching into anterior and lateral cutaneous branches 35 and 37, respectively. Because cuff electrode 17 is located higher (upstream in the central nervous system) from cuff electrode 16, patient 10 may experience paresthesia over a larger area, which may be advantageous in some instances.

In general, cuff electrodes 16 and 17 may be particularly advantageous because cuff electrodes 16 and 17 may remain in place as patient 10 moves without requiring any external fixation means such as sutures or anchoring mechanisms. External fixation means may damage tissue or the nerve itself, possibly causing additional pain which may reduce the efficacy of the electrical stimulation therapy. Cuff electrodes 16 and 17 include a fixation structure that at least partially wraps around iliohypogastric nerve 33. The fixation structure may be fabricated from a flexible biocompatible material that provides a flexible interface between the electrode and iliohypogastric nerve 31.

In some embodiments, the cuff fixation structure may be fabricated from a flexible or rigid biocompatible material. In such cases, the fixation structure may form a split cylinder or a "U" shape sized to fit around iliohypogastric nerve 33. Cuff electrodes 16 and 17 may generally comprise a rigid cuff electrode, a self-sizing spiral cuff electrode, a half cuff electrode, a helical electrode, a chambered electrode, and other types of cuff electrodes that at least partially wrap around one of iliohypogastric nerves 32 and 33. Upon enclosure of at least a portion of iliohypogastric nerves 32 and 33, a cuff may be held in a closed position by shape memory properties, sutures, interlocking tabs, surgical adhesive, crimping, or other fixation techniques or structures.

Figure 3A:
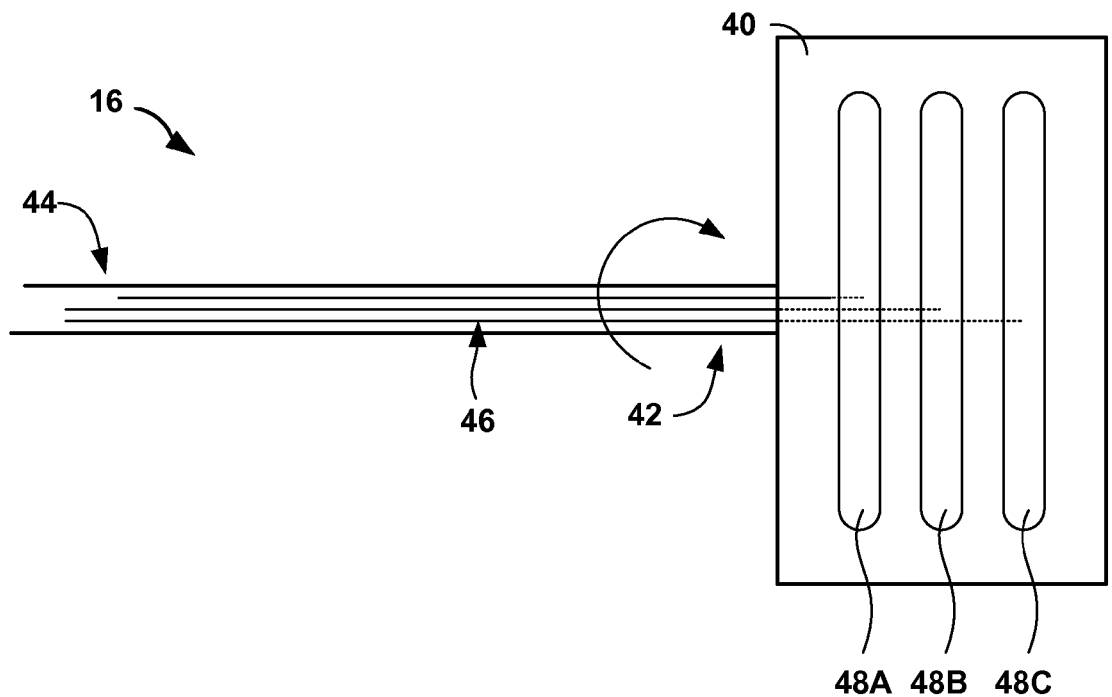
FIGS. 3A, 3B and 3C are schematic diagrams illustrating an example cuff electrode useful in the system of FIGS. 1 and 2.
Figures 3B, 3C:
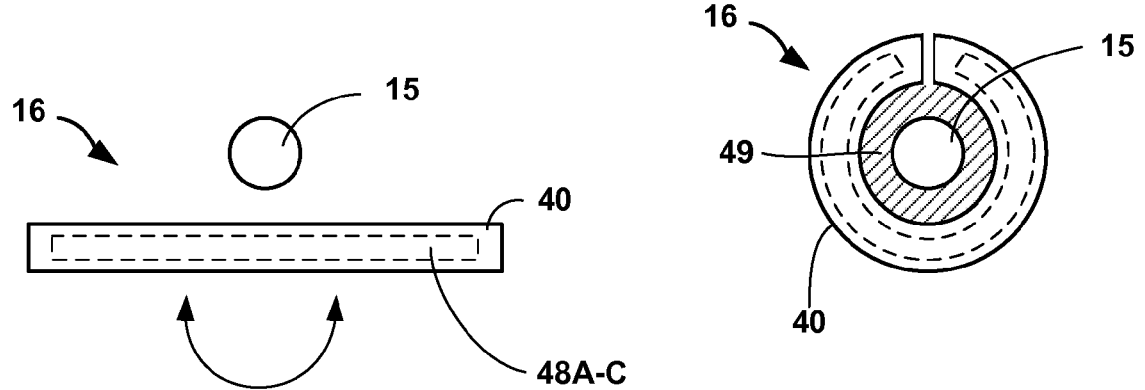

FIGS. 3A, 3B and 3C are schematic diagrams illustrating an exemplary embodiment of a cuff electrode 16. Cuff electrode 17 may be similarly constructed. Cuff electrodes 16 and 17 may be any type of cuff electrode used to deliver electrical stimulation. In some embodiments, cuff electrodes 16 and 17 may both comprise the same type of cuff electrode or may comprise different types of cuff electrodes. In any case, cuff electrode 16 is merely exemplary and should not be considered limiting of the invention as broadly embodied and described in this disclosure. The purpose of FIGS. 3A-C is to illustrate the implantation of cuff electrodes to deliver electrical stimulation to the iliohypogastric nerves.

FIG. 3A is a top view of cuff electrode 16. Cuff electrode 16 includes lead 18, fixation structure 40, a plurality of stimulation electrodes 48A-C, and a plurality of electrical conductors 46 within lead 18. In the example of FIG. 3A, cuff electrode 16 includes three electrodes 48A, 48B, 48C. In the illustrated example, electrodes 48A-C is arranged such that a major axis of each electrode extends laterally to the iliohypogastric nerve. In this manner, the length of each electrode may be wrapped about all or a portion of the circumference of the iliohypogastric nerve. The proximal end 44 of lead 18 is connected to IMD 28 and fixation structure 40 is attached to the distal end 42 of lead 18. Cuff electrode 16 may generally include one electrode or a plurality of electrodes.

Each of electrodes 48A-C is coupled to one of a plurality of supply conductors 46. Electrodes 48A-C may be driven together via a common conductor or independently via separate conductors. When electrodes 48A-C are driven by a common conductor, they may be referenced to one or more electrodes carried by another lead or one or more electrodes carried by the IMD housing. When electrodes 48A-C are driven by separate conductors, bipolar or multipolar electrode combinations may be formed on a single lead or among two or more leads, as well as between one or more leads and the IMD housing.

For a given bipolar pair of electrodes on a lead, one supply conductor sources stimulation energy to a first electrode and a second supply conductor sinks stimulation energy from a second electrode, with the stimulation energy propagating across nerve tissue between the first and second electrodes. Hence, one electrode may form a cathode while the other forms an anode. Also, in some embodiments, multiple anodes and cathodes may be used in an electrode combination. A switch device in the IMD determines which electrodes will function as anodes and which electrodes will function as anodes.

As previously described, fixation structure 40 may be fabricated from a flexible biocompatible material that provides a flexible interface between the electrode and the iliohypogastric nerve. In some embodiments, fixation structure 40 may be fabricated from a rigid biocompatible material. The rigid fixation structure may form a split cylinder or a "U" shape sized to fit around the iliohypogastric nerve. In any case, when implanting electrode 16, the surgeon may elevate the iliohypogastric nerve and wrap fixation structure 40 around the iliohypogastric nerve.

The manner in which the surgeon installs the cuff electrode around the iliohypogastric nerve depends on the type of cuff electrode. For example, if fixation structure 40 is fabricated from a shape memory alloy, fixation structure 40 may recover its shape at a fixed temperature, e.g., slightly under room temperature. By sufficiently cooling fixation structure 40, the surgeon can easily open the cuff and position fixation structure 40 under the iliohypogastric nerve. Because the nominal body temperature of the patient is above room temperature, fixation structure 40 warms up and recovers its initial shape thereby closing or wrapping fixation structure 40 around the iliohypogastric nerve. In another example, the fixation structure may be constrained in a flat manner using a surgical tool or hand and, when released, wraps around the nerve.

FIG. 3B is a cross sectional view of cuff electrode 16 implanted underneath iliohypogastric nerve 33. In the illustrated example, fixation structure 40 is flat thereby allowing the surgeon to easily position electrode 16 under iliohypogastric nerve 33. When fixation structure 40 is fabricated from a shape memory alloy material, the surgeon may cool fixation structure 40 prior to positioning fixation structure 40 to easily manipulate fixation structure 40 into the open configuration shown in FIG. 3B. The surgeon may then position fixation structure under iliohypogastric nerve 33. Fixation structure 40 will recover its initial shape, i.e., a substantially closed ring sized to fit around iliohypogastric nerve 31, as fixation structure warms up to its activation temperature.

FIG. 3C is a cross sectional via of cuff electrode 16 implanted and wrapped around iliohypogastric nerve 33. More specifically, FIG. 3C illustrates the shape of fixation structure 40 when it has returned to its initial shape in response to warming from the patient's body heat. In the illustrated example, a gap 49 may exist between iliohypogastric nerve 33 and fixation structure 40. The gap may be filled with tissue or fluids and may provide a buffer that prevents cuff electrode 16 from damaging iliohypogastric nerve 33. Alternatively, fixation structure 40 may be sized to wrap around iliohypogastric nerve 33 such that there is substantially no gap between fixation structure 40 and iliohypogastric nerve 33. In some embodiments, fixation structure may be deployed using superelastic properties of a shape memory allow such as Nitinol. For example, the fixation structure may be constrained in a flat shape either manually or with a surgical took, and then released so that it wraps around the nerve.

Figure 4:
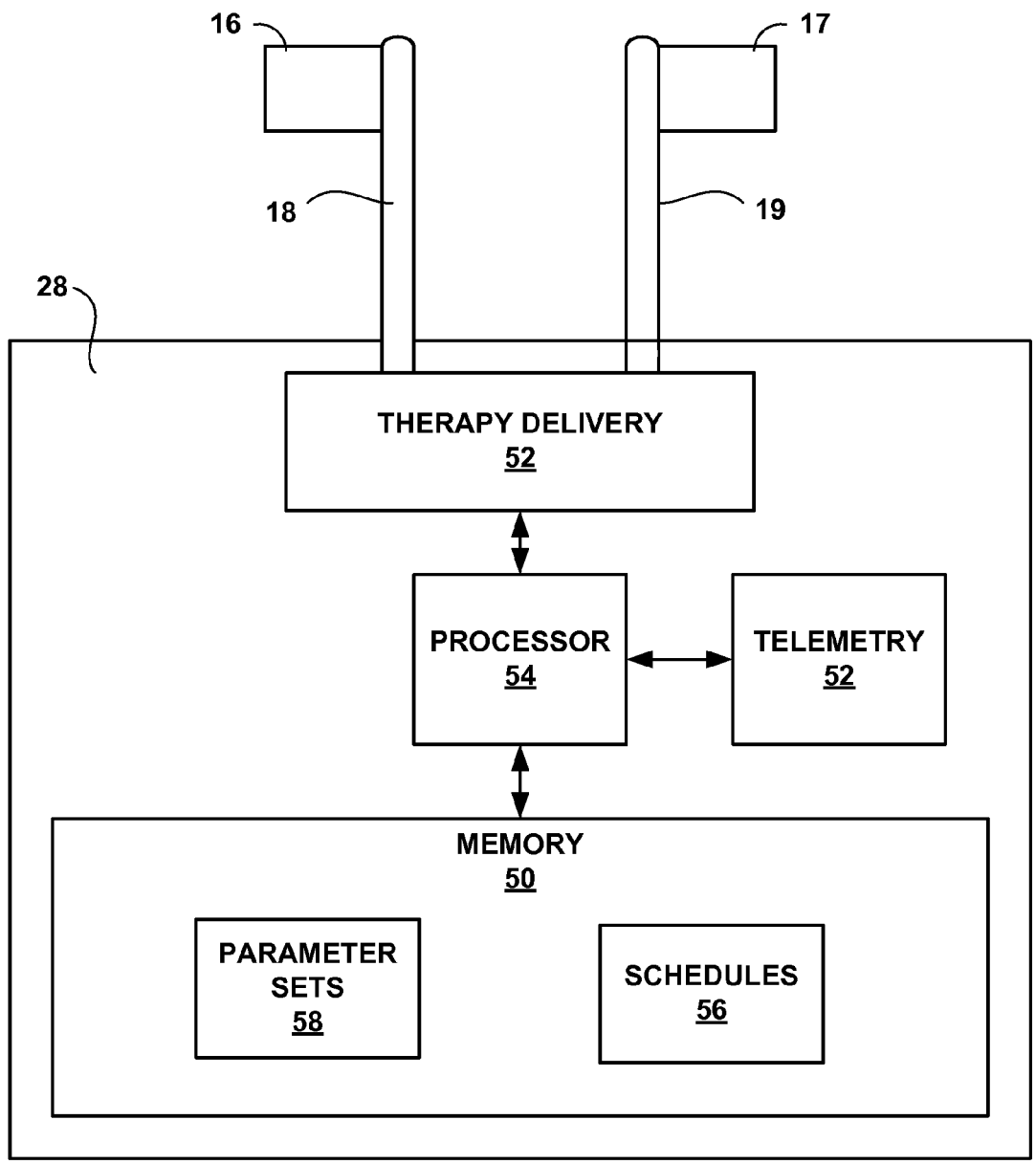
FIG. 4 is a block diagram illustrating an example implantable stimulation device for applying electrical stimulation to the iliohypogastric nerve of a patient.

FIG. 4 is a block diagram illustrating an example configuration of IMD 28. IMD 28 may apply electrical stimulation to iliohypogastric nerves 32 and 33 of patient 10 via electrodes, e.g., electrodes 16 and 17, coupled to IMD 28 via leads 18 and 19, respectively. The configuration, type, and number of electrodes illustrated in FIG. 4 are merely exemplary. Leadless stimulators alternatively may be used instead of or in addition to leads 18, 19 and electrodes 16, 17. A leadless stimulator does not generally include any elongated leads, and instead carries electrodes on a housing of the stimulator or on a structure such as a fixation device extending from the housing.

In the example of FIG. 4, electrodes 16 and 17 are electrically coupled to a therapy delivery module 52 via leads 18 and 19, respectively. Therapy delivery module 52 may, for example, include an output pulse generator coupled to a power source such as a battery and charge storage capacitor. Therapy delivery module 52 may deliver electrical stimulation pulses to patient 10 via one or both of electrodes 16 and 17 under the control of a processor 54.

Processor 54 controls therapy delivery module 52 to deliver electrical stimulation according to a selected parameter set stored in memory 56. Specifically, processor 54 may control circuit 52 to deliver electrical stimulation pulses with the amplitudes and widths, and at the rates specified by the programs of the selected parameter set. Processor 54 may also control circuit 52 to deliver each pulse according to a different program of the parameter set. Processor 54 may include a microprocessor, a controller, a digital signal processor (DSP), an application specific integrated circuit (ASIC), a field programmable gate array (FPGA), or any other equivalent integrated or discrete logic circuitry, or the like.

In some embodiments, memory 50 may store parameter sets 58 that are available to be selected by patient 10 for delivery of electrical stimulation. Memory 50 may also store schedules 56. Memory 50 may include any combination of volatile, non-volatile, fixed, removable, magnetic, optical, or solid state media, such as a random access memory (RAM), random access memory (ROM), CD-ROM, hard disk, removable magnetic disk, memory cards, non-volatile RAM (NVRAM), electrically programmable ROM (EEPROM), flash memory, and the like.

IMD 28 delivers stimulation according to preprogrammed stimulation parameters and, optionally, schedules stored in memory 50. Schedules 56 may define times for processor 54 to select particular parameter sets 58 and control therapy delivery module to delivery therapy according to that parameter set. A schedule 56 may cause electrical stimulation to be delivered via electrodes 16 and 17 at respective times, which may include simultaneous and/or alternate delivery. For example, stimulation may be activated, deactivated or altered for different times of the day, such as times during which the patient is awake or sleeping, or working or at rest. A clinician or patient may create, modify, and select schedules 56 using external programmer 29.

IMD 28 also includes a telemetry circuit 53 that allows processor 54 to communicate with external programmer 29, i.e., a clinician programmer or patient programmer. Processor 54 may receive programs to test on patient 10 from external programmer 29 via telemetry circuit 52 during programming by a clinician. Where IMD 28 stores parameter sets 58 in memory 50, processor 54 may receive parameter sets 58 from external programmer 29 via telemetry circuit 52 during programming by a clinician, and later receive parameter set selections made by patient 10 from external programmer 29 via telemetry circuit 52. Where external programmer 29 stores the parameter sets, processor 54 may receive parameter sets selected by patient 10 from external programmer 29 via telemetry circuit 52.

Figure 5:
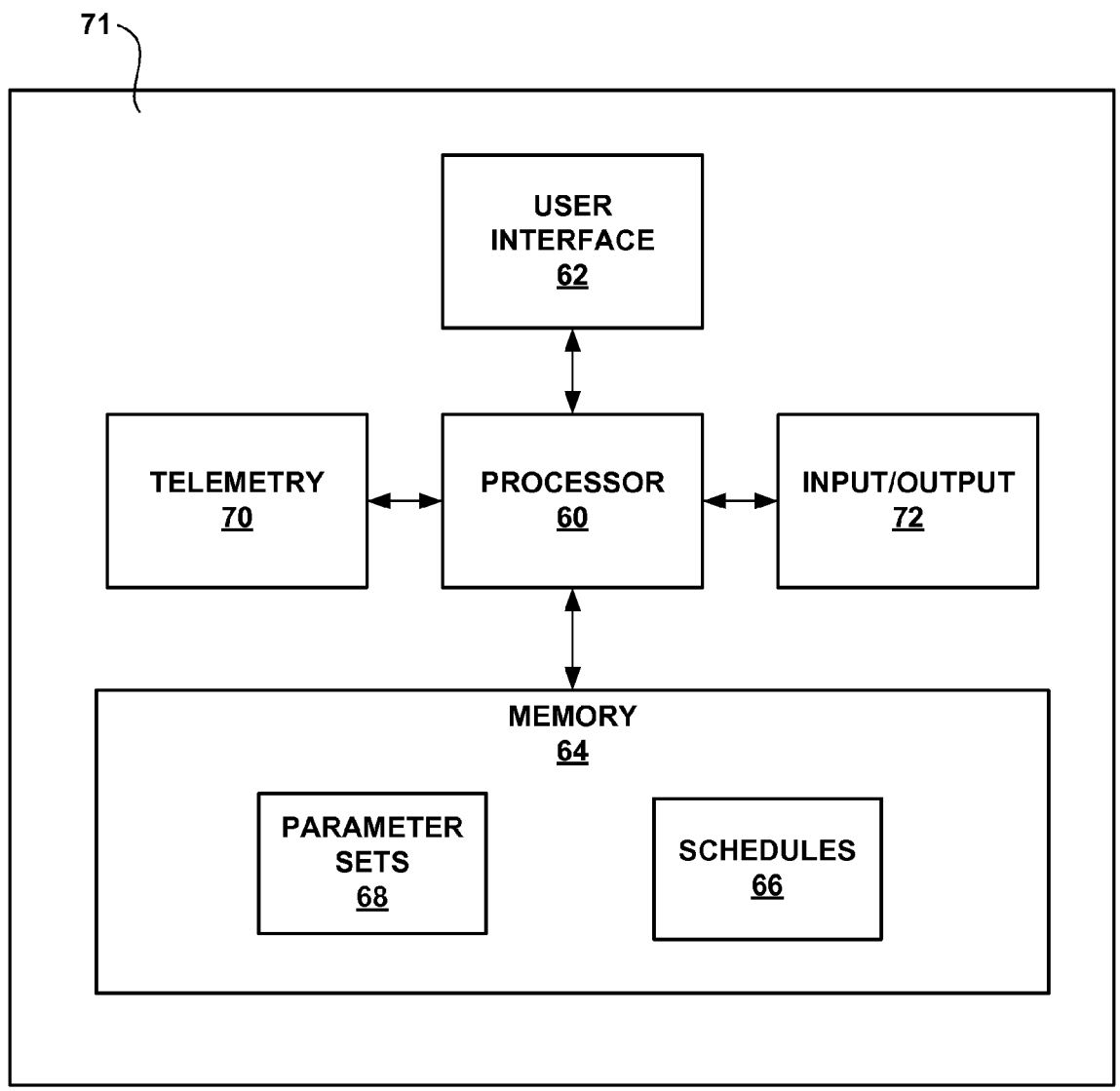
FIG. 5 is a block diagram illustrating an example clinician programmer that allows a clinician to program electrical stimulation therapy for a patient.

FIG. 5 is a block diagram illustrating an example patient or clinician programmer 71 that allows a patient or clinician to program electrical stimulation therapy for a patient. Patient 10 or a clinician may interact with a processor 60 via a user interface 62 in order to control delivery of electrical therapy as described herein. User interface 62 may include a display and a keypad, and may also include a touch screen or peripheral pointing devices as described above. Processor 60 may also provide a graphical user interface (GUI) to facilitate interaction with patient 10, as will be described in greater detail below. Processor 60 may include a microprocessor, a controller, a DSP, an ASIC, an FPGA, discrete logic circuitry, or the like.

Programmer 71 also includes a memory 64. In some embodiments, memory 64 may store parameter sets 68 that are available to be selected by patient 10 or a clinician for delivery of electrical stimulation. Memory 64 may also store schedules 66. Hence, parameter sets and schedules may be stored in IMD 28, programmer 71, or both. Programmer 71 also includes a telemetry circuit 70 that allows processor 60 to communicate with IMD 28, and, optionally, input/output circuitry 72 (e.g., wired or wireless I/O media) to allow processor 60 to communicate with another programmer.

Processor 60 may receive parameter set selections made by patient 10 or a clinician via user interface 62, and may either transmit the selection or the selected parameter set to IMD 28 via telemetry circuitry 70 for delivery of electrical stimulation according to the selected parameter set. Where programmer 71 stores parameter sets 66 in memory 64, processor 60 may receive parameter sets 66 from another programmer via input/output circuitry 72 during programming by a clinician. Circuitry 72 may include transceivers for wireless communication, appropriate ports for wired communication or communication via removable electrical media, or appropriate drives for communication via removable magnetic or optical media.

FIG. 6 is a schematic diagram illustrating another example system 100 for applying electrical stimulation to a male patient 10 for pelvic pain such as chronic groin pain, post vasectomy pain, iliohypogastric neuralgia, and other conditions that cause long term (chronic) pain in the testicles, groin, or abdomen. System 100 also may be useful for alleviation of pelvic pain for female patients. In the illustrated example, system 100 includes electrodes 104 deployed on a lead extending from an IMD 108, and a leadless microstimulator 106. Electrodes 104 and leadless microstimulator 106 deliver electrical stimulation to iliohypogastric nerves 33 and 32, respectively, and illustrate alternative stimulation arrangements. Hence, stimulation energy may be delivered to iliohypogastric nerves 32, 33 via any combination of cuff electrodes, axial electrode arrays (i.e., with ring electrodes), planar electrode array (e.g., on paddle lead), leadless microstimulators, or other types of electrodes.

IMD 108 controls the delivery of electrical stimulation according to preprogrammed stimulation programs, parameter sets and/or schedules. In particular, IMD 108 or external programmer 109 may wirelessly control microstimulator 106 to deliver electrical stimulation to iliohypogastric nerve 30. Alternatively, microstimulator 106 may operate autonomously or in a coordinated manner in conjunction with other microstimulators or IMD 108. In the example of FIG. 6, IMD 108 is also coupled to electrodes 104 via lead 102. Again, the invention is not limited to the illustrated configuration. In general, IMD 108 may be coupled to any number and type of electrodes or electrical stimulators. The electrodes may also be positioned adjacent to one or both iliohypogastric nerves 32, 33 based on the perceived pain of patient 10. However, FIG. 6 illustrates example system 100 in which microstimulator 106 and electrodes 104 deliver bi-lateral electrical stimulation to iliohypogastric nerves 32 and 33, respectively.

In the illustrated example, microstimulator 106 is implanted adjacent to iliohypogastric nerve 32 and includes a housing and a fixation structure attached to the housing. The housing may be formed into a capsule-like shape and may be constructed from any of a variety of biocompatible materials, such as titanium or stainless steel. As will be described, the housing may carry an implantable pulse generator (IPG) and, optionally, a telemetry interface to exchange (send, receive or both) control signals with other devices such as IMD 108 or external programmer 109. The fixation structure on microstimulator 106 may be constructed similar to the fixation structure of previously described cuff electrodes 16 and 17. For example, the fixation structure on microstimulator 106 may be constructed of a flexible or a rigid biocompatible material that at least partially wraps around iliohypogastric nerve 32. The fixation structure may carry one or more electrodes, i.e., the electrodes may be integrated with the fixation structure, and the housing may include short leads that extend from the housing to couple the electrodes to the housing.

Alternatively, leadless microstimulator 106 may be implanted within tissue proximate or adjacent to iliohypogastric nerve 32 using a needle (not shown). In particular, microstimulator 106 may be implanted with a minimally invasive, percutaneous procedure. As an example, the needle may include a hollow cylinder and a pointed distal end for puncturing skin of patient 10. The needle may include the microstimulator and a fluid, e.g., saline solution, or push rod to force the microstimulator out of the needle. In this case, microstimulator 106 may be miniaturized in order to be implanted using the needle. In some embodiments, a plurality of microstimulators may be implanted within tissue proximate to the iliohypogastric nerve. The plurality of implanted microstimulators may apply electrical stimulation independently or on a coordinated basis.

When implanted within tissue proximate to iliohypogastric nerve 32, microstimulator 106 may comprise a self-contained module. The module comprises a housing that may carry one or more electrodes and an IPG within the housing. The IPG may comprise a circuit board and a power source, such as a battery, to provide power to the circuit board and electrodes. The circuit board may include the telemetry interface and other processing electronics. The electrodes may be pads mounted on a surface of the housing or ring electrodes that extend about the entire periphery of the housing. In some cases, the housing itself may form an active "can" electrode in addition to the electrodes mounted on the housing.

Microstimulator 106 may be implanted with less invasive procedures than other electrodes that are coupled to an IMD via a lead. For example, because microstimulator 106 may include a self-contained stimulation pulse generator and one or more electrodes, a surgeon does not have to tunnel a lead to IMD 108. In some embodiments, microstimulator 106 may wirelessly communicate with external programmer 109. In this case, external programmer 109 may be a small, battery-powered, portable device that may accompany patient 10 through the day. External programmer 109 may have a simple user interface, such as a button or keypad, and a display or lights. Patient 10 may only be able to activate and deactivate IMD 108. However, in other embodiments, external programmer 109 may include additional functionality to operate in a manner similar to a patient programmer.

In the illustrated example, ring electrodes 104 mounted on lead 102 also may be used to deliver electrical stimulation to iliohypogastric nerve 33. Lead 102 is coupled to IMD 108 and carries electrical conductors to transmit stimulation energy from the IMD to the electrodes 104 on a selective basis. In particular, one or more electrodes may be selected to form anodes and cathodes for delivery of stimulation energy via unipolar, bipolar or multipolar electrode combinations. Lead 102 may be implanted adjacent to iliohypogastric nerve 33 as shown. Lead 102 is shown in FIG. 6 carrying four electrodes, e.g., ring electrodes, although any number of electrodes could be used. Also, as mentioned previously, electrodes 104 may be arranged in an axial array, e.g., as ring electrodes, or in a two-dimensional planar array, e.g., in a paddle lead. Also, other types of leads providing curved or rounded electrode arrays may be used. At least one conductor is included in lead 102 that electrically connects the proximal end of lead 102 to electrodes 104 in its distal end. IMD 108 may control electrical stimulation applied by each of electrodes 104 separately or control electrical stimulation applied by a group of electrodes 104.

In some embodiments, lead 102 may be formed to include fixation elements, such as hooks, barbs, helical structures, tissue ingrowth mechanisms, or other anchoring mechanisms, e.g., at a distal end of lead 102. Fixation elements may serve to fix electrodes 104, relative to iliohypogastric nerve 33 so that electrodes 104 can provide consistent electrical simulation. Without anchoring electrodes 104 to iliohypogastric nerve 33 or tissue proximate to iliohypogastric nerve 33, the distance between electrodes 104 and iliohypogastric nerve 33 may vary as patient 10 moves throughout the day, reducing the efficacy of the applied electrical stimulation. However, it is possible that anchoring mechanisms may damage iliohypogastric nerve 33 or surrounding tissue during implantation or as patient 10 moves.

System 100 generally operates in a similar manner to system 2 in FIG. 1 to apply electrical stimulation for chronic groin pain, iliohypogastric neuralgia, or other pelvic pain disorders. Accordingly, external programmer 109 may comprise a clinician programmer or a patient programmer. As shown, external programmer 109 may communicate via wireless communication with IMD 108. In particular, external programmer 109 may control delivery of electrical stimulation by IMD 108 using telemetry techniques known in the art. When microstimulator 106 comprises a self-contained module, external programmer 109 may directly communicate with microstimulator 106 via wireless communication to control delivery of electrical stimulation.

Figure 7:
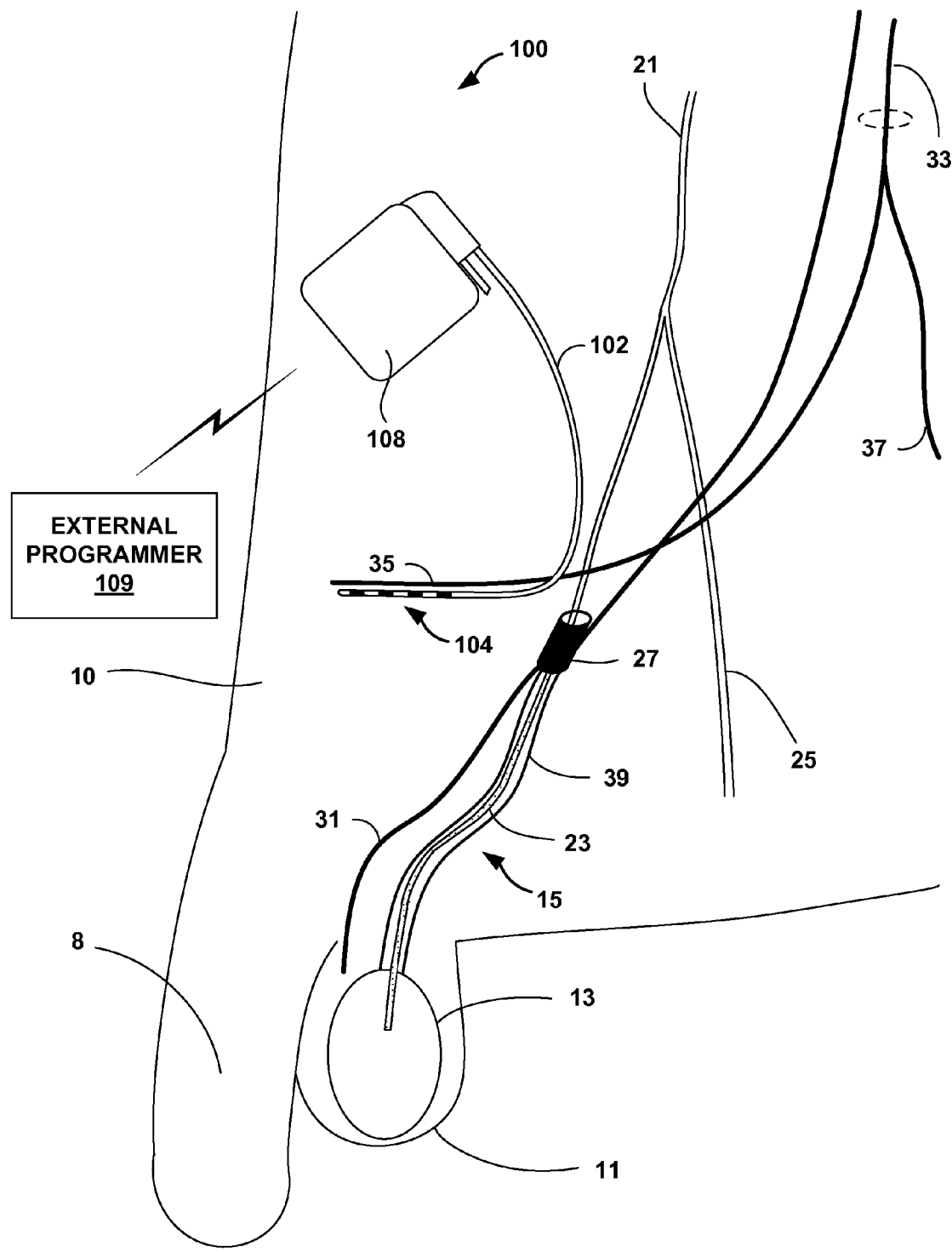
FIG. 7 is a schematic diagram further illustrating the example system of FIG. 6 from a side view of a male patient.

FIG. 7 is a schematic diagram further illustrating example system 100. In particular, system 100 is illustrated from the left side of a male patient 10 in FIG. 7. For purposes of illustration, only iliohypogastric nerve 33, anterior cutaneous branch 35 and lateral cutaneous branch 37 of iliohypogastric nerve 33, genitofemoral nerve 21, genital nerve branch 23 and femoral nerve branch 25 of genitofemoral nerve 21, spermatic cord 15, and testicle 13 are shown. Again, iliohypogastric nerve 33 originates from the L1 and T12 and also, in some cases, the L2 nerve. Iliohypogastric nerve 33 innervates penis 8, scrotum 11, and the skin of the hypogastric and gluteal region of patient 10. In some cases, branches of iliohypogastric nerve 33 may also innervate ilioinguinal nerve 31.

In general, electrical stimulation is applied to iliohypogastric nerve 33 through electrodes 104 of lead 102 implanted adjacent to iliohypogastric nerve 33. More specifically, electrodes 104 of lead 102 are implanted adjacent to anterior cutaneous branch 35 of iliohypogastric nerve 33. Electrodes 104 apply electrical stimulation to iliohypogastric nerve 33 under control of IMD 108. Lead 102 carries electrodes 104 and couples electrodes 104 to IMD 108. In particular, at least one electrical conductor is included in lead 102 that electrically connects electrodes 104 to IMD 108. Electrodes 104 may comprise four electrodes, e.g., ring electrodes, although the invention is not so limited. Electrodes 104 may comprise any number and type of electrodes. In some embodiments, as mentioned above, lead 102 also may include fixation elements, such as hooks, barbs, helical structures, tissue ingrowth mechanisms, or other anchoring mechanisms that aid in securing lead 102 to iliohypogastric nerve 33 or tissue proximate to iliohypogastric nerve 33. Securing lead 102 to iliohypogastric nerve 33 or to tissue proximate to iliohypogastric nerve 33 may prevent lead 102 from moving relative to iliohypogastric nerve 33.

IMD 108 is programmed to deliver electrical stimulation appropriate for chronic groin pain, post vasectomy pain, iliohypogastric neuralgia, and other conditions that cause long term (chronic) pain in the testicles, groin, or abdomen. IMD 108 may control electrical stimulation applied by each of electrodes 104 independently. Alternatively, IMD 108 may control electrical stimulation applied by a group of electrodes 104, and may select different combinations of electrodes 104 in bipolar or multi-polar arrangements to identify a particular combination that is most effective in producing desired paresthesia. Again, IMD 108 may control delivery of electrical stimulation according to parameter sets and/or schedules programmed in internal memory.

Although FIG. 7 illustrates lead 102 implanted adjacent to anterior cutaneous branch 35 of iliohypogastric nerve 33, lead 102 may be implanted adjacent to lateral cutaneous branch 37 of iliohypogastric nerve 33, or a portion of iliohypogastric nerve 33 above the branch point. Again, the region to which electrical stimulation is applied is determined by the pain experienced by the patient. Applying electrical stimulation to iliohypogastric nerve 33 at a location further upstream may cause patient 10 to experience a larger area of paresthesia in response to electrical stimulation. In both male and female patients, stimulation may be applied to any portion of iliohypogastric nerve 33.

Figure 8A:
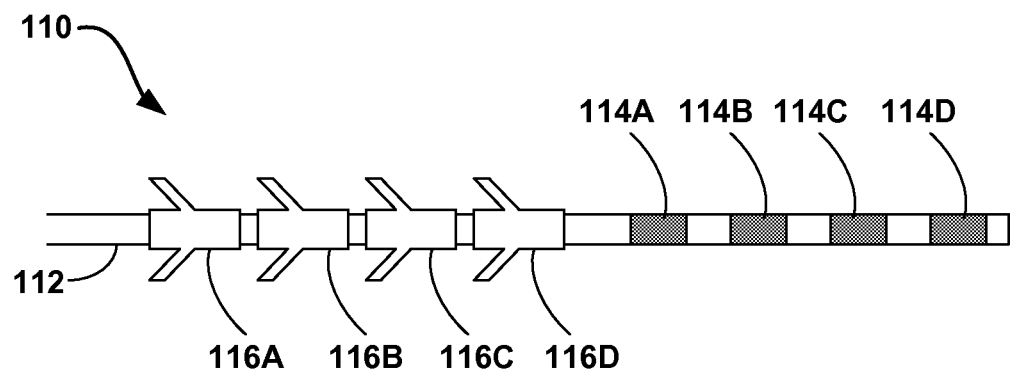
FIGS. 8A and 8B are schematic diagrams illustrating an example electrode lead of FIGS. 6 and 7.
Figure 8B:
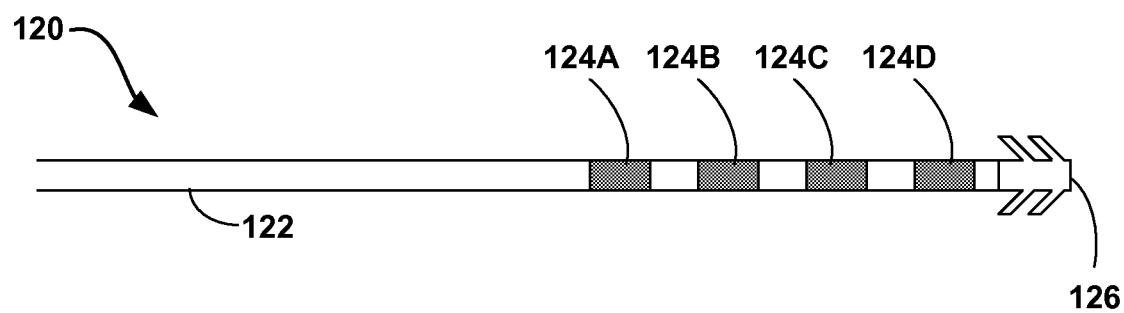

FIGS. 8A and 8B show exemplary electrical leads with fixation elements to secure the lead within a patient. As shown in FIG. 8A, lead 110 includes lead body 112, tines 116A-D (collectively tines 116) and electrodes 114A-D (collectively electrodes 114). Lead 110 may be a standard lead that includes all four tines 116 close to electrodes 114. Lead 110 may be implemented with any number of electrodes or tines. When implanting lead 110, having tines 116 close to electrodes 114 may be beneficial by allowing less movement of electrodes 114 with respect to the iliohypogastric nerve.

Electrodes 114 are more effective in delivering electrical stimulation when the electrodes are located close to the iliohypogastric nerve. If electrodes 114 migrate away from the iliohypogastric nerve, due to movement of the patient throughout the day, for example, the efficacy of the stimulation may decrease. Therefore, tines 116 located close to electrodes 114 may be beneficial to therapy efficacy.

FIG. 8B illustrates a lead 120 which includes lead body 122, tines 126, and electrodes 124A-D (collectively electrodes 124). Lead 120 may be a standard lead that includes tines 126 located at the distal end of lead body 122. Lead 120 may be implemented with any number of electrodes or tines. Electrodes 124 may be located close to or a distance away from tines 126. When electrodes 124 are close to tines 126, implanting lead 120 may allow less movement of electrodes 124 with respect to the iliohypogastric nerve. Consequently, the intensity of electrical stimulation delivered to the iliohypogastric nerve may not vary and cause the patient to experience different levels of paresthesia.

When electrodes 124 are located a distance away from tines 126, implanting lead 102 may allow electrodes 124 to reach further away from the anchoring site. For example, when lead 102 delivers electrical stimulation to the iliohypogastric nerve, tines may be anchored to tissue a distance away from the iliohypogastric nerve while leads may be located proximate to the iliohypogastric nerve. Securing tines 126 to the iliohypogastric nerve is undesirable because the nerve may be damaged in the process. Thus, lead 120 may be beneficial by preventing unwanted nerve damage during the implantation process.

Figure 9:
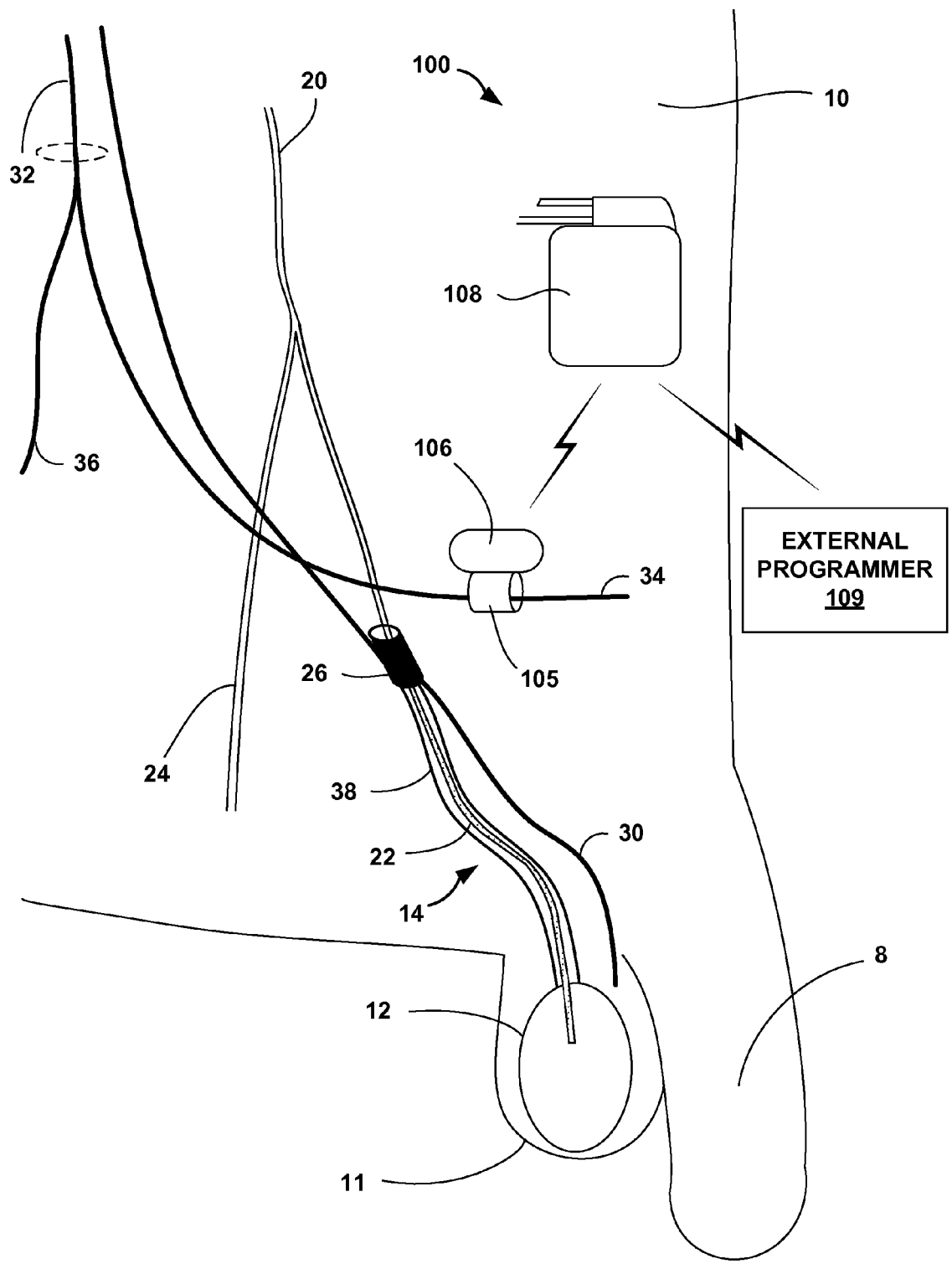
FIG. 9 is a schematic diagram further illustrating the example system of FIG. 6.

FIG. 9 is a schematic diagram further illustrating example system 100. In particular, system 100 is illustrated from the right side of a male patient 10. For purposes of illustration, only iliohypogastric nerve 32, anterior cutaneous branch 34 and lateral cutaneous branch 36 of iliohypogastric nerve 32, genitofemoral nerve 20, genital nerve branch 22 and femoral nerve branch 24 of genitofemoral nerve 20, spermatic cord 14, testicle 12, and scrotum 11 are shown. As previously described and similar to iliohypogastric nerve 33, iliohypogastric nerve 32 originates from the L1 and T12 and also, in some cases, the L2 nerve. Iliohypogastric nerve 32 innervates penis 8, scrotum 11, and the skin of the hypogastric and gluteal region of patient 10. In some cases, branches of iliohypogastric nerve 32 may also innervate inguinal nerve 30.

Microstimulator 106 applies electrical stimulation to iliohypogastric nerve 32 under control of IMD 108 or external programmer 109. As shown, IMD 108 or external programmer 109 may wirelessly control microstimulator 106 to delivery electrical stimulation. Microelectrode 106 includes a housing 107 and a fixation structure 105, such as a cuff, attached to housing 107. Housing 107 may be formed into a capsule-like shape and may be constructed from any of a variety of biocompatible materials, such as titanium. Housing 107 may carry an implantable pulse generator (IPG) and a telemetry interface to receive control signals from IMD 108. Fixation structure 105 wraps at least partially around iliohypogastric nerve 32 to secure microstimulator 106 in place. Accordingly, fixation structure 105 may operate and be constructed similar to the fixation structure of previously described cuff electrodes 16 and 17. Fixation structure 105 may carry one or more electrodes coupled to housing 107 via short leads (not shown). In some embodiments, housing 107 may form an active "can" electrode.

The invention is not limited to the illustrated configuration, i.e., microstimulator 106 implanted to deliver electrical stimulation to anterior cutaneous branch 34. For example, microstimulator 106 may also be implanted, additionally or alternatively, to deliver electrical stimulation to lateral cutaneous branch 36 and iliohypogastric nerve 32 above the branch point. In such cases, fixation structure 105 wraps at least partially around lateral cutaneous branch 36 and iliohypogastric nerve 32, respectively. In addition, in some embodiments, a microstimulator may be implanted to deliver electrical stimulation at both locations in a coordinated manner or independently of each other.

FIGS. 10A-10C are enlarged schematic diagrams showing microstimulator 106. In particular, FIG. 10A is an enlarged top view of microstimulator 106 including housing 107, circuit board 130, power supply 132, fixation structure 105, and electrodes 108A-C (collectively electrodes 108). Housing 107 may have a rounded, capsule-like shape, and a smooth, atraumatic surface formed of one or more biocompatible materials, such as titanium, stainless steel, epoxy, or polyvinylchloride. However, the invention is not so limited. Instead, housing 107 may have a shape that is compatible with the anatomy at the implant site, i.e., the iliohypogastric nerve. In some embodiments, the leadless microstimulator may have a capsule shape with a diameter of approximately less than or equal to 2 cm and a length of less than or equal to approximately 5 cm.

Fixation structure 105 may be constructed of a flexible or rigid biocompatible material that at least partially wraps around the iliohypogastric nerve, e.g., like a cuff. For example, fixation structure 105 may be fabricated from a shape memory alloy that has the capacity to recover a memorized shape when deformed at a certain temperature and then heated at a higher temperature or vice versa. In this case, the memorized shape may be a split cylinder or a substantially closed cylinder with a diameter sized to wrap around the iliohypogastric nerve.

FIG. 10A illustrates fixation structure 105 in a deformed, generally open state that enables a surgeon to easily position slip microstimulator 106 underneath the iliohypogastric nerve. However, after positioning microstimulator 106 beneath the spermatic cord, the body temperature of the patient causes fixation structure 105 to recover its memorized shape, i.e., a split cylinder. Therefore, fixation structure 105 may be beneficial by reducing trauma during surgical implantation procedures.

Fixation structure 105 also carries one or more electrodes 108. Electrodes 108 may be driven together or independently. For example, electrodes 108 may be selectively driven to form combinations of anodes and cathodes. Electrodes 108 may be integrated with fixation structure 105 or, alternatively housing 107 may include short leads (not shown) that extend from housing 107 to couple electrodes 108 to housing 107.

Circuit board 130 may include a processor, memory, pulse generator circuitry to generate electrical pulses delivered by 108, and telemetry circuitry for wireless telemetry with IMD 108, external programmer 109, or both. As an example, the memory may store stimulation parameters, e.g., electrode polarity, pulse width, pulse rate, and amplitude. Memory may also store schedules which define times for the processor to select particular parameters. A schedule may cause electrical stimulation to be delivered at respective times. In this manner, the processor may control the pulse generator circuitry generate electrical stimulation pulses in accordance with the selected parameters and schedule.

Microstimulator 106 may also operate under control from an external programmer, so that a physician or patient may activate, deactivate and/or modify stimulation delivered to the patient on a selective basis. Power source 132 supplies operating power to circuit board 130 and may take the form of a small rechargeable or non-rechargeable battery. Different types of batteries or different battery sizes may be used. To promote longevity, power source 132 may be rechargeable via induction or other means.

FIG. 10B illustrates a cross sectional view of microstimulator 106 implanted underneath iliohypogastric nerve 32. In the illustrated example, fixation structure 105 is flat, thereby allowing the surgeon to easily position microelectrode 106 underneath iliohypogastric nerve 32. When fabricated from a shape memory alloy, the body temperature of patient 10 may heat fixation structure 105 above the recovery shape temperature. In another example, the fixation structure may be constrained in a flat manner using a surgical tool or hand and, when released, wraps around the nerve.

FIG. 10C is a cross sectional view of microelectrode 106 with fixations structure 105 wrapped substantially around iliohypogastric nerve 32. For example, as fixation structure 105 is warmed above its recovery shape temperature, fixation structure 105 recovers its initial shape, i.e., a substantially closed cylinder or ring. As shown in FIG. 10C, in some embodiments, fixation structure 105 may not close completely. However, fixation structure 105 may at least wrap partially around iliohypogastric nerve 32 in order to secure microstimulator 106 to the nerve site. Removing microelectrode 106 may be easier when fixation structure 105 does not completely wrap around iliohypogastric nerve 32 because the gap between the ends of fixation structure 105 may provide an area to insert a tool that aids in removal. In alternative embodiments, fixation structure 105 may wrap completely around iliohypogastric nerve 32.

In the illustrated example, a gap 109 exists between iliohypogastric nerve 32 and fixation structure 105. Gap 109 may be filled with tissue or fluids and may provide a buffer that prevents microstimulator 106 from damaging iliohypogastric nerve 32. Alternatively, fixation structure 105 may be sized to wrap around iliohypogastric nerve 32 such that there is substantially no gap between fixation structure 105 and iliohypogastric nerve 32.

Figure 11:
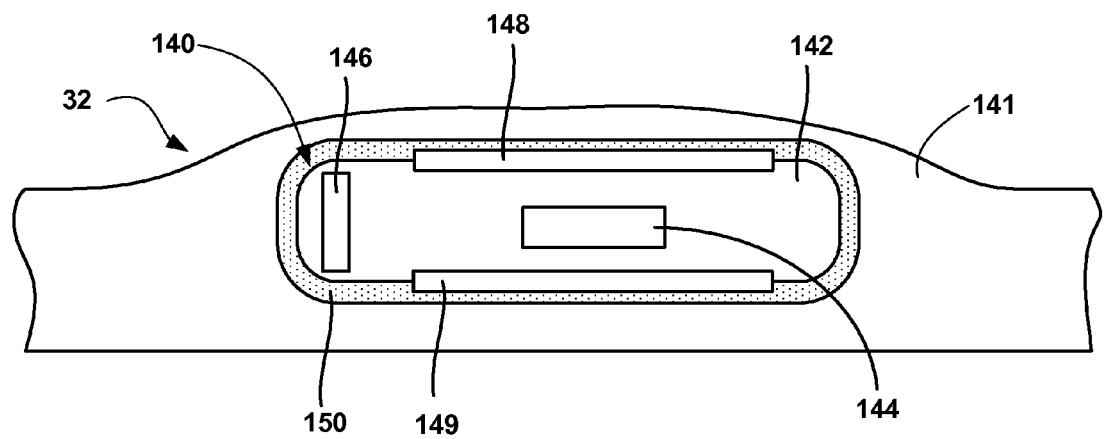
FIG. 11 is a side cross-sectional view of a leadless electrical microstimulator implanted within tissue proximate to the iliohypogastric nerve of a patient.
Figure 12:
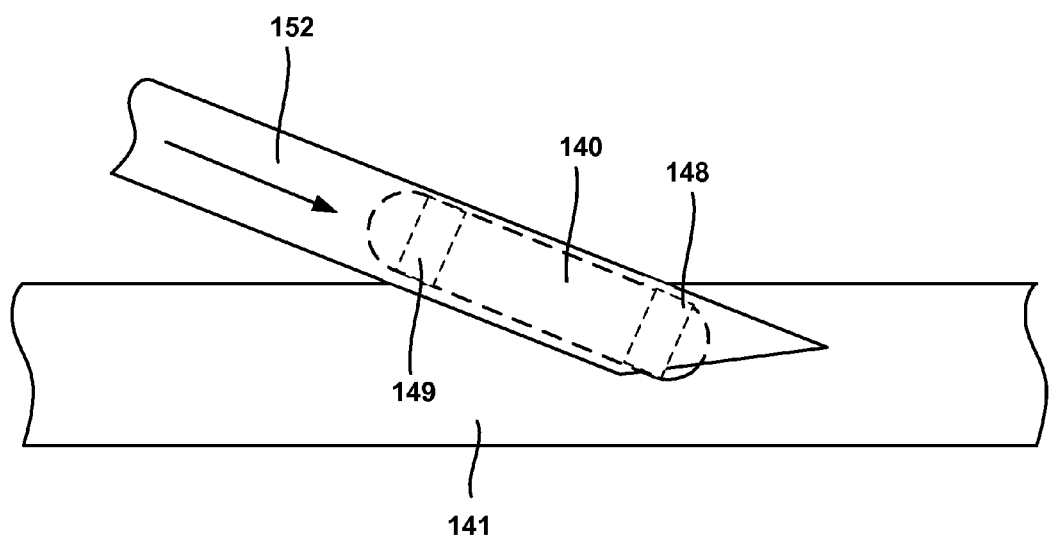
FIG. 12 is a schematic diagram illustrating implantation of a leadless microstimulator within tissue proximate to the iliohypogastric nerve.

FIG. 11 is cross-sectional view of a microstimulator 140 implanted within, for example, tissue 141 proximate or adjacent to iliohypogastric nerve 32. Housing 142 of microstimulator 140 is embedded in tissue 141 proximate to iliohypogastric nerve 32 and includes circuit board 144, power source 146, and electrodes 148 and 149. Housing 142 is in the shape of a rounded capsule and includes a smooth surface. The only structure extending from housing 142 are electrodes 148 and 149. Electrodes 148 and 149 may protrude slightly from housing 142 or, alternatively, may be integrated into housing 142 to apply electrical stimulation to tissue 141. Electrodes 148 and 149 may be constructed as pads, as shown in FIG. 11, or as ring electrodes, as shown in FIG. 12. Microstimulator 140 rests in wall cavity 150 formed within external fascia 141. As previously described, microstimulator 140 may have a cylindrical shape with a diameter of less than or equal to approximately 2 cm and a length of less than or equal to approximately 5 cm.

Circuit board 144, power source 146, and electrodes 148 and 149 may be similar to respective circuit board 130, power source 132, and electrodes 108 of FIGS. 11A-C. Differences between these components of each embodiment may relate to the size or shape of each component. Therefore, electrodes 148 and 149 apply electrical stimulation under control of circuit board 144. Power source supplies operating power to circuit board 144. Circuit board 144 may select stimulation parameters and cause electrodes 148 and 149 to apply electrical pulses with the selected parameters according to schedules stored in memory. Circuit board 140 receives control signals from IMD 108, external programmer 109, or both by wireless telemetry. In some embodiments, one of electrodes 148 and 149 may comprise a sensor or microstimulator 140 may additionally include a sensor that detects a physiological parameter. In such embodiments, the sensor may sense a change in a physiological parameter. Processing electronics on circuit board 144 detects the change and causes electrodes to apply electrical stimulation in response to the change.

Implanting microstimulator 140 within tissue 141 proximate to iliohypogastric nerve 32 may be a simple method for securing electrodes 148 and 149. In some embodiments, a plurality of microstimulators similar to microstimulator 140 may be implanted and apply electrical stimulation to iliohypogastric nerve 32 in a coordinated manner or in a manner independent of each other.

FIG. 12 is a schematic diagram illustrating implantation of microstimulator 140 within tissue 141 of iliohypogastric nerve 32. Microstimulator 140 may be implanted through endoscopic, laparoscopic, or similar minimally invasive techniques. A surgeon may make a small inguinal incision in patient 10 and guides microstimulator 140 within needle 152 to tissue 141. Needle 152 may be constructed of a metal alloy and comprise a hollow cylinder and a pointed distal end for puncturing the skin of patient 10. Needle 152 includes microstimulator 140 and a fluid or push rod to force microstimulator 140 out of the needle. An exemplary fluid may be saline or other biocompatible fluid.

Once needle 152 in positioned at the appropriate location with respect to iliohypogastric nerve 32, the surgeon may force microstimulator 140 into place. Removing needle 152 from tissue 141 proximate to iliohypogastric nerve 32 allows tissue 141 to close and surround microstimulator 140. When implanting microstimulator 140, tissue 141 should not be breached in order to prevent iliohypogastric nerve 32 from being damaged.

In other embodiments, microstimulator 140 may be implanted through more invasive procedures which expose iliohypogastric nerve 32. As previously described, multiple microstimulators may be implanted in tissue 141 proximate to iliohypogastric nerve 32 to apply electrical stimulation to a larger area.

Figure 13:
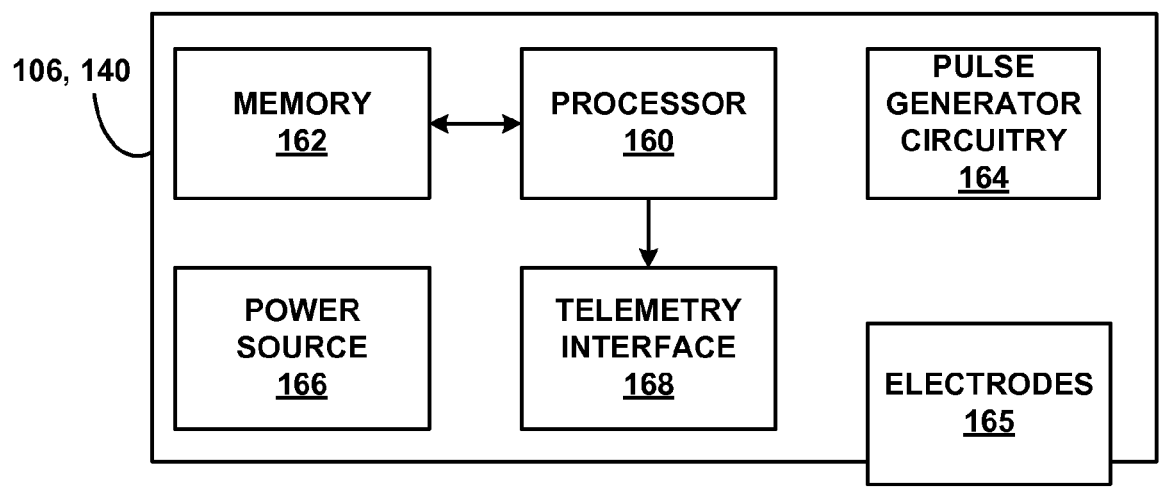
FIG. 13 is a functional block diagram illustrating various components of the leadless microstimulator of FIG. 11.

FIG. 13 is a functional block diagram illustrating various components of an example microstimulator 106 (FIG. 6) or microstimulator 140 (FIG. 11). In the example of FIG. 9, microstimulator 140 includes a processor 160, memory 162, pulse generator circuitry 164, telemetry interface 168, power source 166 and electrodes 165. Pulse generator circuitry 164 may be carried on a circuit board, along with processor 160, memory 162, and telemetry interface 168. Memory 162 may store instructions for execution by processor 160, stimulation parameters, e.g., electrode polarity, pulse width, pulse rate, and amplitude, and schedules for delivering electrical stimulation. Memory 162 may include separate memories for storing instructions, stimulation parameter sets, and schedules. Memory 162 may comprise any form of computer-readable media such as magnetic or optical tape or disks, solid state volatile or non-volatile memory, including random access memory (RAM), read only memory (ROM), electronically programmable memory (EPROM or EEPROM), or flash memory.

Processor 160 controls pulse generator circuitry 164 to deliver electrical stimulation via electrodes 165. Electrodes 165 may comprise any number and type of electrodes previously described, i.e., electrodes 108 (FIG. 6) and electrodes 148 and 149 (FIG. 11). An exemplary range of stimulation pulse parameters likely to be effective in treating post vasectomy pain, iliohypogastric neuralgia, and other conditions that cause long term pain in the testicles, groin, or abdomen when applied to the iliohypogastric nerve are as follows: pulse widths between approximately 10 and 5000 microseconds, more preferably between approximately 100 and 1000 microseconds and still more preferably between 180 and 450 microseconds; voltage amplitudes between approximately 0.1 and 50 volts, more preferably between approximately 0.5 and 20 volts and still more preferably between approximately 1 and 10 volts; and frequencies between approximately 0.5 and 500 hertz, more preferably between approximately 10 and 250 hertz and still more preferably between approximately 50 and 150 hertz. The pulses may be alternating current (ac) pulses or direct current (dc) pulses, and may be mono-phasic, bi-phasic, or multi-phasic in various embodiments.

Processor 160 also controls telemetry interface 168 to receive information from IMD 108, external programmer 109, or both. Telemetry interface 168 may communicate via wireless telemetry, e.g., RF communication, on a continuous basis, at periodic intervals, or upon request from the implantable stimulator or programmer. Processor 160 may include a single or multiple processors that are realized by microprocessors, Application-Specific Integrated Circuits (ASIC), Field-Programmable Gate Arrays (FPGA), or other equivalent integrated or discrete logic circuitry.

Power source 166 delivers operating power to the components of the implantable microstimulator. As mentioned previously, power source 166 may include a small rechargeable or non-rechargeable battery and a power generation circuit to produce the operating power.

Figure 14:
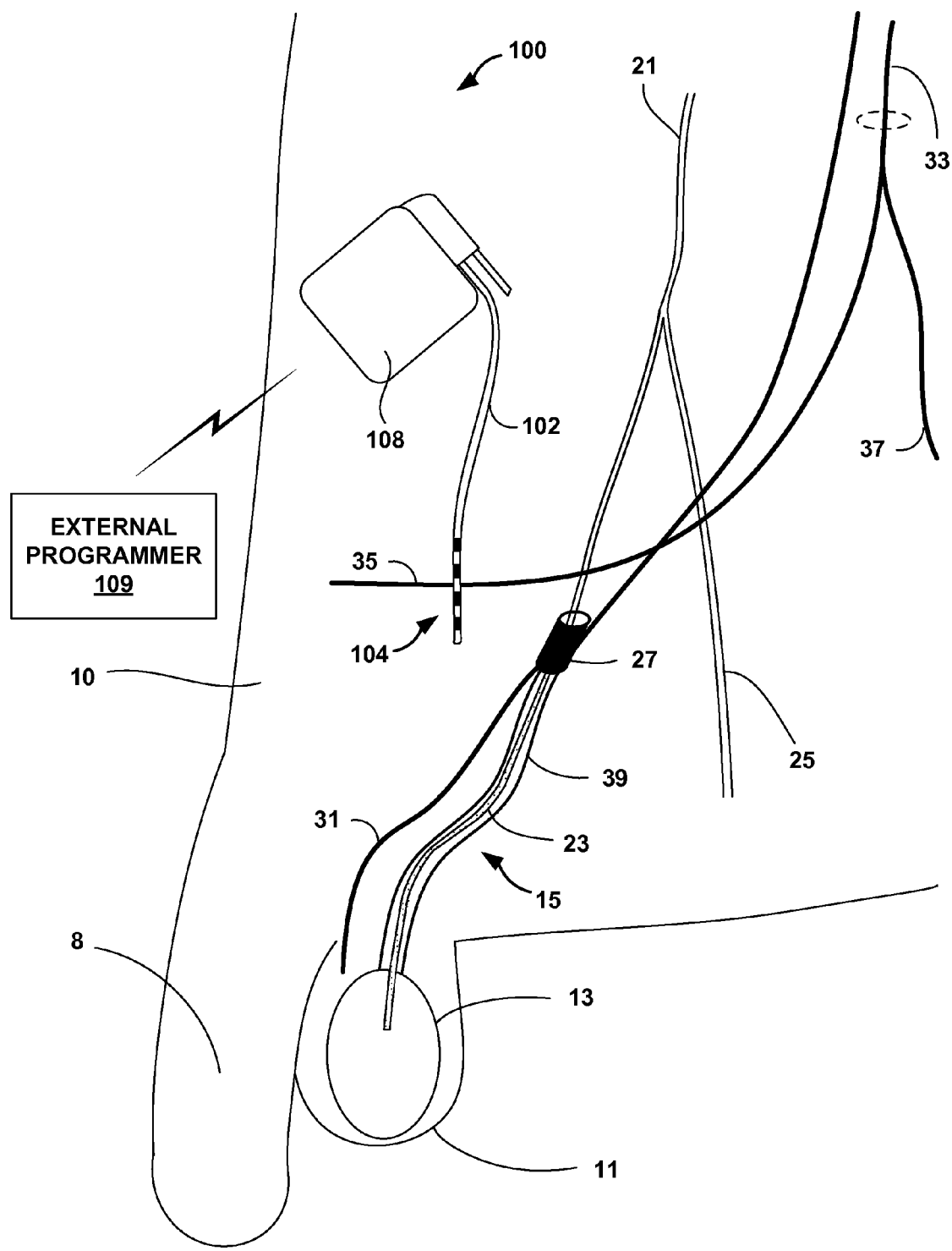
FIG. 14 is a schematic diagram illustrating another configuration for the example system of FIG. 7.

FIG. 14 is a schematic diagram illustrating another configuration for example system 100 of FIG. 7. In particular, rather than being implanted along iliohypogastric nerve 33, electrodes 104 are illustrated in FIG. 14 as being implanted perpendicular to iliohypogastric nerve 33. Implanting electrodes 104 perpendicular to iliohypogastric nerve 33 may provide certain advantages. For example, when implanted as shown, electrodes 104 may more effectively apply electrical stimulation to a point along iliohypogastric nerve 33 instead of applying electrical stimulation along a length or portion of iliohypogastric nerve 33. Patient 10 may experience a more complete relief of pain or fewer unwanted side effects as a result of applying electrical stimulation in this manner. The invention is not limited to the illustrated embodiments. Instead, electrodes 104 may be implanted at any orientation with respect to iliohypogastric nerve 33.

Figure 15:
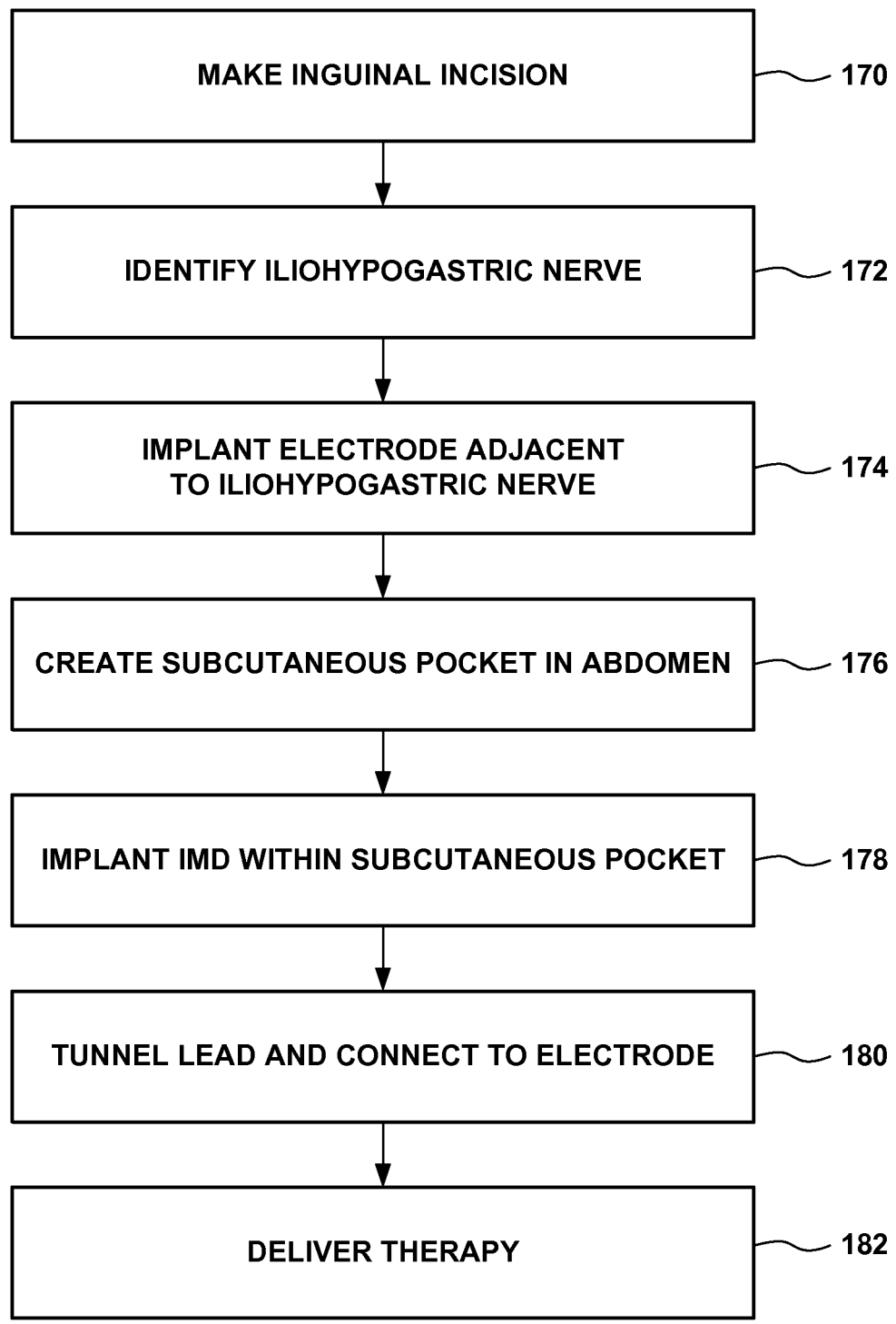
FIG. 15 is a flow chart illustrating a technique for applying electrical stimulation to an iliohypogastric nerve of a patient for alleviation of pelvic pain.

FIG. 15 is a flow chart illustrating a technique for applying electrical stimulation to an iliohypogastric nerve of a patient using an implantable electrode. Any of the previously described electrodes, i.e., cuff electrodes 16 and 17 (FIG. 1), electrodes 104 carried by lead 102 (FIG. 6), microstimulator 106 (FIG. 6), and microstimulator 140 (FIG. 7), may be implanted in accordance with the steps of the illustrated flow chart. The flow of events begins with the surgical procedure for implanting the electrode. The surgical procedure for exposing the iliohypogastric nerve for lead placement is well defined and may be used. Specifically, the surgeon makes an inguinal incision (170) as used for standard iliohypogastric denervation or hernia repair.

The surgeon identifies the iliohypogastric nerve (172) and implants an electrode adjacent to the iliohypogastric nerve (174). When implanting a cuff electrode, the surgeon may elevate the iliohypogastric nerve and wrap the cuff electrode around the iliohypogastric nerve. If the fixation structure of the cuff electrode is formed from a shape memory alloy, the body temperature of the patient may cause the fixation structure to recover its initial shape, i.e., a substantially closed cylinder or ring shape sized to fit around the iliohypogastric nerve. In any case, the cuff electrode may wrap at least partially around the iliohypogastric nerve thereby securing the cuff electrode to the iliohypogastric nerve.

When implanting lead 102 carrying electrodes 104, fixation elements such as hooks, barbs, helical structures, tissue ingrowth mechanisms, or other anchoring mechanisms may secure lead 102 to the iliohypogastric nerve or tissue proximate to the iliohypogastric nerve. Leads carrying electrodes may provide distinct advantages due to the number of electrodes available to apply electrical stimulation. For example, leads are available that carry eight, sixteen, or more electrodes which can be used to apply electrical stimulation in various groups or independently of each other. Further, because the electrodes may be positioned along a substantial length of the lead, the electrodes may apply electrical stimulation along a larger area of the iliohypogastric nerve.

The surgeon may implant microstimulator 106 similar to cuff electrodes 16 and 17 because the fixation structure of microstimulator 106 may operate in the same manner as the fixation structure of cuff electrodes 16 and 17. In contrast, the surgeon may implant microstimulator 140 within tissue proximate or adjacent to the iliohypogastric nerve using a needle. The needle may comprise a hollow cylinder and a pointed distal end for puncturing the skin of the patient and a fluid to force microstimulator 140 out of the needle. Accordingly, the surgeon may not need to make an inguinal incision when implanting microstimulator 140 within the tissue proximate to the iliohypogastric nerve. Rather, once the needle is positioned at the appropriate location with respect to the iliohypogastric nerve, the surgeon forces microstimulator 140 into place by depressing the plunger of the needle thereby forcing the fluid and microstimulator out of the needle.

Removing the needle from the tissue allows the tissue to close and surround microstimulator 140. Consequently, microstimulator 140 may be implanted with a minimally invasive surgical procedure. Additionally, in some embodiments, the surgeon may implant a plurality of microstimulators along the iliohypogastric nerve. The microstimulators may provide electrical stimulation independently or on a coordinated basis.

In general, the implantation techniques may be used to implant electrodes proximate to an anterior or lateral cutaneous branch of one or both iliohypogastric nerves or one or both iliohypogastric nerves, i.e., above the branch point of the iliohypogastric nerves. Implanting an electrode proximate to a region of the iliohypogastric nerve above the branch point may provide paresthesia to a larger area of the patient because electrical stimulation is applied further upstream of the central nervous system (CNS).

In any case, after implanting the electrode, the surgeon may create a subcutaneous pocket in the abdomen of the patient (176) and implant an IMD, such as IMD 28 (FIG. 1) or IMD 108 (FIG. 6), within the subcutaneous pocket (178). In some embodiments, the IMD may be miniaturized and implanted within the scrotum of the patient. The surgeon may then tunnel the electrode lead through the tissue in the patient to the implantation site and connect the lead to the implanted electrode(s) (180). Notably, microstimulators 106 and 140 may wirelessly communicate with external programmer 109 to receive control signals and, thus, not require an IMD.

When the surgical implantation procedure is complete, the implanted electrodes may apply electrical stimulation to deliver therapy (182) the iliohypogastric nerve. Applying electrical stimulation to the iliohypogastric nerve may block pain signals from the penis, testicles, and the associated scrotal area from reaching the CNS. The pain experienced by the patient may be uni-lateral or bi-lateral. Consequently, electrodes may be implanted adjacent to one or both iliohypogastric nerves of a patient. The pain experienced by the patient may also be constant or intermittent, or spontaneous or exacerbated by physical activities and pressure. Thus, the implanted electrodes may apply electrical stimulation on demand, such as in response to a control signal received from a patient or clinician programmer, or in accordance with preprogrammed cycles or schedules.

Electrical stimulation of the iliohypogastric nerve may provide may provide substantial relief of pelvic pain experienced by male and female patients, including urogenital pain or other forms of pelvic pain. In male patients, for example, electrical stimulation of the iliohypogastric nerve may relieve a variety of pelvic pain conditions such as chronic groin pain, post vasectomy pain, iliohypogastric neuralgia, and other conditions that cause long term (chronic) pain in the testicles, groin, or abdomen. For female patients, electrical stimulation of the iliohypogastric nerve may alleviate a variety of pelvic pain conditions such as pain resulting from surgical procedures, vulvodynia, interstitial cystitis (painful bladder syndrome), adhesions, endometriosis, and pelvic congestion. Accordingly, although the invention has been primarily described with respect to male patients, the invention is not so limited and may be readily applied to female patients for similar relief of pain symptoms.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure Many embodiments of the invention have been described. Various modifications may be made without departing from the scope of the claims. These and other embodiments are within the scope of the following claims.

The invention claimed is:

1. A system comprising:
an implantable stimulation device configured to generate electrical stimulation selected to alleviate pelvic pain; and
a processor configured to control the implantable stimulation device to apply the electrical stimulation to at least one of an anterior cutaneous nerve branch and a lateral cutaneous nerve branch of an iliohypogastric nerve of a patient at a point after the iliohypogastric nerve has branched to form the anterior cutaneous nerve branch and the lateral cutaneous nerve branch.

2. The system of claim 1, wherein the processor is configured to control the implantable stimulation device to apply electrical stimulation to the iliohypogastric nerve at a point prior to the iliohypogastric nerve branching to form the anterior cutaneous nerve branch and the lateral cutaneous nerve branch.

3. The system of claim 2, wherein the processor is configured to control the implantable stimulation device to apply the electrical stimulation, on an alternating basis, at the points prior to and after the iliohypogastric nerve branches to form the anterior cutaneous nerve branch and the lateral cutaneous nerve branch.

4. The system of claim 1, wherein the electrical stimulation comprises first electrical stimulation and the iliohypogastric nerve comprises a first iliohypogastric nerve, wherein the implantable stimulation device is further configured to generate second electrical stimulation selected to alleviate pelvic pain, and wherein the processor is further configured to control the implantable stimulation device to deliver the second electrical stimulation to a second iliohypogastric nerve of the patient.

5. The system of claim 4, wherein the processor is configured to control the implantable stimulation device to apply the first and second electrical stimulation on an alternating basis.

6. The system of claim 4, wherein the processor is configured to control the implantable stimulation device to apply the second electrical stimulation to at least one of an anterior cutaneous nerve branch and a lateral cutaneous nerve branch of the second iliohypogastric nerve of the patient at a point after the second iliohypogastric nerve has branched to form the anterior cutaneous nerve branch and the lateral cutaneous nerve branch of the second iliohypogastric nerve.

7. The system of claim 6, wherein the processor is configured to control the implantable stimulation device to apply, on an alternating basis, the first electrical stimulation to the at least one of the anterior cutaneous nerve branch and the lateral cutaneous nerve branch of the first iliohypogastric nerve and the second electrical stimulation to the at least one of the anterior cutaneous nerve branch and the lateral cutaneous nerve branch of the second iliohypogastric nerve.

8. The system of claim 1, wherein the implantable stimulation device is configured to generate the electrical stimulation that is selected to alleviate pelvic pain comprising at least one of chronic groin pain, chronic testicular pain (CTP), post vasectomy pain, iliohypogastric neuralgia, vulvodynia, and interstitial cystitis.

9. The system of claim 1, further comprising an electrode coupled to the implantable stimulation device, wherein the electrode includes at least one of a cuff electrode, a ring electrode, a planar electrode, and an electrode on a leadless stimulator.

10. The system of claim 9, wherein the electrode includes a cuff electrode including a cuff-like fixation structure and one or more electrodes.

11. The system of claim 10, further comprising an implantable medical lead coupled to the implantable stimulation device, wherein the cuff electrode is mounted to the implantable medical lead.

12. The system of claim 10, wherein the implantable stimulation device comprises a leadless stimulator, and wherein the cuff electrode is mounted to the leadless stimulator.

13. The system of claim 1, wherein the implantable stimulation device includes a leadless stimulator configured to be at least partially implanted within tissue proximate to the iliohypogastric nerve of the patient.

14. A system comprising:
means for generating electrical stimulation selected to alleviate pelvic pain of a patient; and
means for applying the electrical stimulation to at least one of an anterior cutaneous nerve branch and a lateral cutaneous nerve branch of an iliohypogastric nerve of a patient at a point after the iliohypogastric nerve has branched to form the anterior cutaneous nerve branch and the lateral cutaneous nerve branch.

15. The system of claim 14, further comprising an electrode, wherein the means for applying electrical stimulation applies the electrical stimulation via the electrode, and wherein the electrode includes at least one of a cuff electrode, a ring electrode, a planar electrode, and an electrode on a leadless stimulator.

16. The system of claim 15, wherein the electrode includes a cuff electrode including a cuff-like fixation structure and one or more electrodes.

17. The system of claim 14, wherein the electrical stimulation comprises first electrical stimulation and the iliohypogastric nerve comprises a first iliohypogastric nerve, the system further comprising:
means for generating second electrical stimulation selected to alleviate pelvic pain of the patient; and
means for applying the second electrical stimulation to a second iliohypogastric nerve of the patient.

18. The system of claim 17, wherein the means for applying the first electrical stimulation and the means for applying the second electrical stimulation apply the first and second electrical stimulation on an alternating basis.

19. A computer-readable storage medium comprising instructions that, when executed, cause a programmable processor to:
control an implantable stimulation device to apply electrical stimulation to at least one of an anterior cutaneous nerve branch and a lateral cutaneous nerve branch of an iliohypogastric nerve of a patient at a point after the iliohypogastric nerve has branched to form the anterior cutaneous nerve branch and the lateral cutaneous nerve branch, wherein the electrical stimulation is selected to alleviate pelvic pain of the patient.

20. The computer-readable storage medium of claim 19, further comprising instructions that, when executed, cause the programmable processor to:
control the implantable stimulation device to apply electrical stimulation to the iliohypogastric nerve at a point prior to the iliohypogastric nerve branching to form the anterior cutaneous nerve branch and the lateral cutaneous nerve branch.

21. The computer-readable storage medium of claim 20, further comprising instructions that, when executed, cause the programmable processor to:
control the implantable stimulation device to apply electrical stimulation, on an alternating basis, at the points prior to and after the iliohypogastric nerve branches to form the anterior cutaneous nerve branch and the lateral cutaneous nerve branch.

22. The computer-readable storage medium of claim 19, wherein the electrical stimulation comprises first electrical stimulation and the iliohypogastric nerve comprises a first iliohypogastric nerve, the computer-readable storage medium further comprising instructions that, when executed, cause the programmable processor to:
control the implantable stimulation device to apply second electrical stimulation to a second iliohypogastric nerve of the patient.

23. The computer-readable storage medium of claim 22, further comprising instructions that, when executed, cause the programmable processor to:
control the implantable stimulation device to apply the first and second electrical stimulation on an alternating basis.

24. The computer-readable storage medium of claim 22, further comprising instructions that, when executed, cause the programmable processor to:
control the implantable stimulation device to apply the second electrical stimulation to at least one of an anterior cutaneous nerve branch and a second lateral cutaneous nerve branch of the second iliohypogastric nerve of the patient at a point after the second iliohypogastric nerve has branched to form the anterior cutaneous nerve branch and the lateral cutaneous nerve branch of the second iliohypogastric nerve.

25. The computer-readable storage medium of claim 24, further comprising instructions that, when executed, cause the programmable processor to:
control the implantable stimulation device to apply electrical stimulation, on an alternating basis, to the at least one of the anterior cutaneous nerve branch and the lateral cutaneous nerve branch of the first iliohypogastric nerve and to the at least one of the anterior cutaneous nerve branch and the lateral cutaneous nerve branch of the second iliohypogastric nerve.

26. The computer-readable storage medium of claim 19, wherein the electrical stimulation is selected to alleviate pelvic pain comprising at least one of chronic groin pain, chronic testicular pain (CTP), post vasectomy pain, iliohypogastric neuralgia, vulvodynia, and interstitial cystitis.

* * * * *